United States Patent [19]
Yates, III et al.

[11] Patent Number: 5,538,897

[45] Date of Patent: Jul. 23, 1996

[54] USE OF MASS SPECTROMETRY FRAGMENTATION PATTERNS OF PEPTIDES TO IDENTIFY AMINO ACID SEQUENCES IN DATABASES

[75] Inventors: John R. Yates, III, Seattle; James K. Eng, Seatac, both of Wash.

[73] Assignee: University of Washington, Seattle, Wash.

[21] Appl. No.: 212,433

[22] Filed: Mar. 14, 1994

[51] Int. Cl.$^6$ ............................................ G01N 33/00
[52] U.S. Cl. .......................... 436/89; 436/94; 436/173; 530/334; 530/335; 530/336; 530/337; 530/402; 530/412; 530/417
[58] Field of Search ............................ 436/89, 94, 173; 530/334–337, 412, 417, 402

[56] References Cited

U.S. PATENT DOCUMENTS

5,240,859 8/1993 Aebersold .............................. 436/89

OTHER PUBLICATIONS

Powell and Heiftje, Anal. Chim. Acta, vol. 100, pp. 313–327 (1978).

Hunt, et al., "Protein Sequencing by Tandem Mass Spectrometry," *Proc. Natl Acad. Sci. USA*, 83:6233–6237 (1986).

Smith, et al., "Collisional Activation and Collision–Activated Dissociation of Large Multiply Charged Polypeptides and Proteins Produced by Electrospray Ionization," *J. Am. Soc. Mass Spectrom.*, 1:53–65 (1990).

Burks, et al., "GenBank: Current Status and Future Directions in Methods in Enzymology," 183:3 (1990).

Kahn, et al., "EMBL Data Library", *Methods in Enzymology*, 183:23 (1990).

Barker, et al., "Protein Sequence Database," *Methods in Enzymology*, 183:31 (1990).

Griffin, et al., "Structural Analysis of Proteins by Capillary HPLC Electrospray Tandem Mass Spectrometry," *Int'l J. Mass Spectrom. and Ion Processes*, 111:131–149 (1991).

McLuckey, et al., "Tandem Mass Spectrometry of Small, Multiply Charged Oligonucleotides," *J. Am. Soc. Mass Spectrom.*, 3:60–70 (1992).

Bairoch, et al., "The Swiss–Prot Protein Sequence Data Bank, Recent Developments," *Nucleic Acids Res.*, 21:3093–3096 (1993).

"Index of the Protein Sequence Database of the International Association of Protein Sequence Databanks (PIR–International)", *Protein Seq. Data Anal.*, 5:67–192 (1993).

(List continued on next page.)

*Primary Examiner*—David A. Redding
*Attorney, Agent, or Firm*—Townsend and Townsend and Crew

[57] ABSTRACT

A method for correlating a peptide fragment mass spectrum with amino acid sequences derived from a database is provided. A peptide is analyzed by a tandem mass spectrometer to yield a peptide fragment mass spectrum. A protein sequence database or a nucleotide sequence database is used to predict one or more fragment spectra for comparison with the experimentally-derived fragment spectrum. In one embodiment, sub-sequences of the sequences found on the database which define a peptide having a mass substantially equal to the mass of the peptide analyzed by the tandem mass spectrometer are identified as candidate sequences. For each candidate sequence, a plurality of fragments of the sequence are identified and the masses and m/z ratios of the fragments are predicted and used to form a predicted mass spectrum. The various predicted mass spectra are compared to the experimentally derived fragment spectrum using a closeness-of-fit measure, preferably calculated with a two-step process, including a calculation of a preliminary score and, for the highest-scoring predicted spectra, calculation of a correlation function.

19 Claims, 10 Drawing Sheets

OTHER PUBLICATIONS

Henzel, et al., "Identifying Proteins from Two–Dimensional Gels by Molecular Mass Searching of Peptide Fragments in Protein Sequence Databases," *Proc. Natl. Acad. Sci. USA,* 90:5011–5015 (Jun. 1993).

Yates, III, et al., "Peptide Mass Maps: A Highly Informative Approach to Protein Identification," *Analytical Biochemistry,* 214:1–12 (1993).

Griffin, et al., "Analysis of Proteins by Mass Spectrometry," *Analysis of Proteins by Mass Spectrometry,* pp. 467–476 (no date).

Yates, III, et al., "Computer Aided Interpretation of Low Energy MS/MS Mass Spectra of Peptides," *Techniques in Protein Chemistry II,* pp. 477–485 (no date).

PREPROCESSING

DATABASE SEARCH

SEARCH

ANALYSIS

CORRELATION ANALYSIS

SEQUENCE LISTING ( 1 ) GENERAL INFORMATION:

( i i i ) NUMBER OF SEQUENCES: 46

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Asp  Leu  Arg  Ser  Trp  Thr  Ala  Ala  Asp  Ala  Ala  Gln  Ile  Ser  Lys
 1                  5                        10                       15
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Asp  Leu  Arg  Ser  Trp  Thr  Ala  Ala  Asp  Ala  Ala  Gln  Ile  Ser  Gln
 1                  5                        10                       15
```

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Asp  Pro  Phe  Ala  Glu  Asp  Asp  Trp  Glu  Ala  Trp  Ser  His
 1                  5                        10
```

( 2 ) INFORMATION FOR SEQ ID NO:4:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Ala Pro Glu Gly Glu Leu Gly Asp Ser Leu Gln Thr Ala Phe Asp Glu
1               5                   10                  15

Gly Lys ( 2 ) INFORMATION FOR SEQ ID NO:5:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Thr Gly Gly Gly Ala Ser Leu Glu Leu Leu Glu Gly Lys
1               5                   10

( 2 ) INFORMATION FOR SEQ ID NO:6:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Gln Ala Phe Asp Asp Ala Ile Ala Glu Leu Asp Thr Leu Ser Glu Glu
1               5                   10                  15

Ser Tyr Lys ( 2 ) INFORMATION FOR SEQ ID NO:7:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Ile Pro Ala Gly Trp Gln Gly Leu Asp Asn Gly Pro Ser Glu Arg
1               5                   10                  15

( 2 ) INFORMATION FOR SEQ ID NO:8:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Leu Pro Gly Thr Asp Val Asp Leu Pro Ala Leu Ser Glu Lys
1               5                   10

( 2 ) INFORMATION FOR SEQ ID NO:9:

( i ) SEQUENCE CHARACTERISTICS:
        ( A ) LENGTH: 18 amino acids
        ( B ) TYPE: amino acid
        ( C ) STRANDEDNESS: single ( D ) TOPOLOGY: linear ( i i ) MOLECULE TYPE: peptide ( x i ) SEQUENCE DESCRIPTION: SEQ ID NO:9:

```
Ile Glu Asp Asp Pro Phe Glu Asn Leu Glu Asp Thr Asp Asp Asp Phe
1               5                   10                  15

Gln Lys
```

( 2 ) INFORMATION FOR SEQ ID NO:10:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Glu Glu Ala Leu Asp Leu Ile Val Asp Ala Ile Lys
1               5                   10
```

( 2 ) INFORMATION FOR SEQ ID NO:11:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Asn Pro Thr Val Glu Val Glu Leu Thr Thr Glu Lys
1               5                   10
```

( 2 ) INFORMATION FOR SEQ ID NO:12:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Asp Leu Arg Ser Trp Thr Ala Ala Asp Thr Ala Ala Gln Ile Ser Gln
1               5                   10                  15
```

( 2 ) INFORMATION FOR SEQ ID NO:13:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Asp Leu Arg Ser Trp Thr Ala Ala Asp Thr Ala Ala Gln Ile Thr Gln
1               5                   10                  15
```

( 2 ) INFORMATION FOR SEQ ID NO:14:

( i ) SEQUENCE CHARACTERISTICS:
        ( A ) LENGTH: 11 amino acids

```
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:14:

Met  Ala  Thr  Pro  Leu  Leu  Met  Gln  Ala  Leu  Pro
   1                   5                        10
```

( 2 ) INFORMATION FOR SEQ ID NO:15:

```
        ( i ) SEQUENCE CHARACTERISTICS:
                ( A ) LENGTH: 14 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:15:

Glu  Gly  Val  Asn  Asp  Asn  Glu  Glu  Gly  Phe  Phe  Ser  Ala  Arg
   1                   5                        10
```

( 2 ) INFORMATION FOR SEQ ID NO:16:

```
        ( i ) SEQUENCE CHARACTERISTICS:
                ( A ) LENGTH: 10 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:16:

Asp  Arg  Val  Tyr  Ile  His  Pro  Phe  His  Leu
   1                   5                        10
```

( 2 ) INFORMATION FOR SEQ ID NO:17:

```
        ( i ) SEQUENCE CHARACTERISTICS:
                ( A ) LENGTH: 15 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:17:

Val  Glu  Ala  Asp  Val  Ala  Gly  His  Gly  Gln  Asp  Ile  Leu  Ile  Arg
   1                   5                        10                        15
```

( 2 ) INFORMATION FOR SEQ ID NO:18:

```
        ( i ) SEQUENCE CHARACTERISTICS:
                ( A ) LENGTH: 14 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:18:

His  Gly  Val  Thr  Val  Leu  Thr  Ala  Leu  Gly  Ala  Ile  Leu  Lys
   1                   5                        10
```

( 2 ) INFORMATION FOR SEQ ID NO:19:

```
        ( i ) SEQUENCE CHARACTERISTICS:
                ( A ) LENGTH: 16 amino acids
```

(B) TYPE: amino acid
(C) STRANDEDNESS: single
(D) TOPOLOGY: linear (ii) MOLECULE TYPE: peptide (xi) SEQUENCE DESCRIPTION: SEQ ID NO:19:

His Ser Gly Gln Ala Glu Gly Tyr Ser Tyr Thr Asp Ala Asn Ile Lys
1               5                   10                  15

(2) INFORMATION FOR SEQ ID NO:20:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:20:

His Ser Gly Gln Ala Glu Gly Tyr
1               5

(2) INFORMATION FOR SEQ ID NO:21:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:21:

Met Ala Phe Gly Gly Leu Lys
1               5

(2) INFORMATION FOR SEQ ID NO:22:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:22:

Gly Ala Thr Leu Phe Lys
1               5

(2) INFORMATION FOR SEQ ID NO:23:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:23:

Thr Glu Phe Lys
1

(2) INFORMATION FOR SEQ ID NO:24:

(i) SEQUENCE CHARACTERISTICS:
    (A) LENGTH: 10 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:24:

Asp Arg Asn Asp Leu Leu Thr Tyr Leu Lys
1               5                   10

(2) INFORMATION FOR SEQ ID NO:25:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:25:

Val Leu Val Leu Asp Thr Asp Tyr Lys Lys
1               5                   10

(2) INFORMATION FOR SEQ ID NO:26:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:26:

Cys Arg Gly Asp Ser Tyr
1               5

(2) INFORMATION FOR SEQ ID NO:27:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:27:

Lys Gly Ala Thr Leu Phe Lys
1               5

(2) INFORMATION FOR SEQ ID NO:28:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:28:

Thr Gly Pro Asn Leu His Gly Leu Phe Gly Arg
1               5                   10

(2) INFORMATION FOR SEQ ID NO:29:

(i) SEQUENCE CHARACTERISTICS:
    (A) LENGTH: 8 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:29:

Asp Arg Val Tyr Ile His Pro Phe
1               5

(2) INFORMATION FOR SEQ ID NO:30:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:30:

Thr Leu Leu Val Gly Glu Ser Ala Thr Thr Phe
1               5                   10

(2) INFORMATION FOR SEQ ID NO:31:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:31:

Arg Asn Val Ile Pro Asp Ser Lys Tyr
1               5

(2) INFORMATION FOR SEQ ID NO:32:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:32:

Ser Ser Pro Leu Pro Leu
1               5

(2) INFORMATION FOR SEQ ID NO:33:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:33:

Leu Ala Arg Asn Cys Gln Pro Asn Tyr Trp
1               5                   10

(2) INFORMATION FOR SEQ ID NO:34:

(i) SEQUENCE CHARACTERISTICS:
(A) LENGTH: 22 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:34:

Ala Gln Ser Met Gly Phe Ile Asn Glu Asp Leu Ser Thr Ser Ala Gln
1               5                   10                  15

Ala Leu Met Ser Asp Trp
            20

(2) INFORMATION FOR SEQ ID NO:35:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:35:

Val Thr Leu Ile His Pro Ile Ala Met Asp Asp Gly Leu Arg
1               5                   10

(2) INFORMATION FOR SEQ ID NO:36:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:36:

Gly Gly Asp Thr Val Thr Leu Asn Glu Thr Asp Leu Thr Gln Ile Pro
1               5                   10                  15

Lys (2) INFORMATION FOR SEQ ID NO:37:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:37:

Val Gly Glu Glu Val Glu Ile Val Gly Ile Lys
1               5                   10

(2) INFORMATION FOR SEQ ID NO:38:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:38:

Gly Trp Gln Val Pro Ala Phe Thr Leu Gly Gly Glu Ala Thr Asp Ile
1               5                   10                  15

Val Val Met Arg
            20

(2) INFORMATION FOR SEQ ID NO:39:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

Val Ala Ser Ile Ser Leu Pro Thr Ser Cys Ala Ser Ala Gly Thr Gln
1               5                   10                  15

Cys Leu Ile Ser Gly Trp Gly Asn Thr Lys
            20                  25

(2) INFORMATION FOR SEQ ID NO:40:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

Ser Ser Gly Thr Ser Tyr Pro Asp Val Leu Lys
1               5                   10

(2) INFORMATION FOR SEQ ID NO:41:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

Thr Leu Asn Asn Asp Ile Met Leu Ile Lys
1               5                   10

(2) INFORMATION FOR SEQ ID NO:42:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

Ser Ile Val His Pro Ser Tyr Asn Ser Asn Thr Leu Asn Asn Asp Ile
1               5                   10                  15

Met Leu Ile Lys
            20

(2) INFORMATION FOR SEQ ID NO:43:

(i) SEQUENCE CHARACTERISTICS:
        (A) LENGTH: 7 amino acids
        (B) TYPE: amino acid
        (C) STRANDEDNESS: single ( D ) TOPOLOGY: linear ( i i ) MOLECULE TYPE: peptide ( x i ) SEQUENCE DESCRIPTION: SEQ ID NO:43:

Asp Leu Arg Ser Trp Thr Ala
1               5

( 2 ) INFORMATION FOR SEQ ID NO:44:

( i ) SEQUENCE CHARACTERISTICS:
　　( A ) LENGTH: 24 base pairs
　　( B ) TYPE: nucleic acid
　　( C ) STRANDEDNESS: single
　　( D ) TOPOLOGY: linear ( i i ) MOLECULE TYPE: peptide ( x i ) SEQUENCE DESCRIPTION: SEQ ID NO:44:

GCGAUCUCCG GUCUUGGACU GCUC                             2 4

( 2 ) INFORMATION FOR SEQ ID NO:45:

( i ) SEQUENCE CHARACTERISTICS:
　　( A ) LENGTH: 8 amino acids
　　( B ) TYPE: amino acid
　　( C ) STRANDEDNESS: single
　　( D ) TOPOLOGY: linear ( i i ) MOLECULE TYPE: peptide ( x i ) SEQUENCE DESCRIPTION: SEQ ID NO:45:

Ala Ile Ser Gly Leu Gly Leu Leu
1               5

( 2 ) INFORMATION FOR SEQ ID NO:46:

( i ) SEQUENCE CHARACTERISTICS:
　　( A ) LENGTH: 7 amino acids
　　( B ) TYPE: amino acid
　　( C ) STRANDEDNESS: single
　　( D ) TOPOLOGY: linear ( i i ) MOLECULE TYPE: peptide ( x i ) SEQUENCE DESCRIPTION: SEQ ID NO:46:

Arg Ser Pro Val Leu Gly Leu
1               5

USE OF MASS SPECTROMETRY FRAGMENTATION PATTERNS OF PEPTIDES TO IDENTIFY AMINO ACID SEQUENCES IN DATABASES

The present invention is directed to mass spectrometry of peptides and, in particular, to correlating fragmentation patterns of peptide fragments obtained from mass spectrometry with amino acid sequences stored in a database.

BACKGROUND OF THE INVENTION

A number of approaches have been used in the past for applying the analytic power of mass spectrometry to peptides. Tandem mass spectrometry (MS/MS) techniques have been particularly useful. In tandem mass spectrometry, the peptide or other input (commonly obtained from a chromatography device) is applied to a first mass spectrometer which serves to select, from a mixture of peptides, a target peptide of a particular mass or molecular weight. The target peptide is then activated or fragmented to produce a mixture of the "target" or parent peptide and various component fragments, typically peptides of smaller mass. This mixture is then applied to a second mass spectrometer which generates a fragment spectrum. This fragment spectrum will typically be expressed in the form of a bar graph having a plurality of peaks, each peak indicating the mass-to-change ratio (m/z) of a detected fragment and having an intensity value.

Although the bare fragment spectrum can be of some interest, it is often desired to use the fragment spectrum to identify the peptide (or the parent protein) which resulted in the fragment mixture. Previous approaches have typically involved using the fragment spectrum as a basis for hypothesizing one or more candidate amino acid sequences. This procedure has typically involved human analysis by a skilled researcher, although at least one automated procedure has been described John Yates, III, et al,. "Computer Aided Interpretation of Low Energy MS/MS Mass Spectra of Peptides" *Techniques In Protein Chemistry II* (1991), pp. 477–485, incorporated herein by reference. The candidate sequences can then be compared with known amino acid sequences of various proteins in the protein sequence libraries.

The procedure which involves hypothesizing candidate amino acid sequences based on fragment spectra is useful in a number of contexts but also has certain difficulties. Interpretation of the fragment spectra so as to produce candidate amino acid sequences is time-consuming, often inaccurate, highly technical and in general can be performed only by a few laboratories with extensive experience in tandem mass spectrometry. Reliance on human interpretation often means that analysis is relatively slow and lacks strict objectivity. Approaches based on peptide mass mapping are limited to peptide masses derived from an intact homogenous protein generated by specific and known proteolytic cleavage and thus are not generally applicable to mixtures of proteins.

Accordingly, it would be useful to provide a system for correlating fragment spectra with known protein sequences while avoiding the delay and/or subjectivity involved in hypothesizing or deducing candidate amino acid sequences from the fragment spectra.

SUMMARY OF THE INVENTION

According to the present invention, known amino acid sequences, e.g., in a protein sequence library, are used to calculate or predict one or more candidate fragment spectra. The predicted fragment spectra are then compared with an experimentally-derived fragment spectrum to determine the best match or matches. Preferably, the parent peptide, from which the fragment spectrum was derived has a known mass. Subsequences of the various sequences in the protein sequence library are analyzed to identify those sub-sequences corresponding to a peptide whose mass is equal to (or within a given tolerance of) the mass of the parent peptide in the fragment spectrum. For each sub-sequence having the proper mass, a predicted fragment spectrum can be calculated, e.g., by calculating masses of various amino acid subsets of the candidate peptide. The result will be a plurality of candidate peptides, each with a predicted fragment spectrum. The predicted fragment spectra can then be compared with the fragment spectrum derived from the tandem mass spectrometer to identify one or more proteins having sub-sequences which are likely to be identical with the sequence of the peptide which resulted in the experimentally-derived fragment spectrum.

DESCRIPTION OF THE PREFERRED EMBODIMENT

Figure 1:
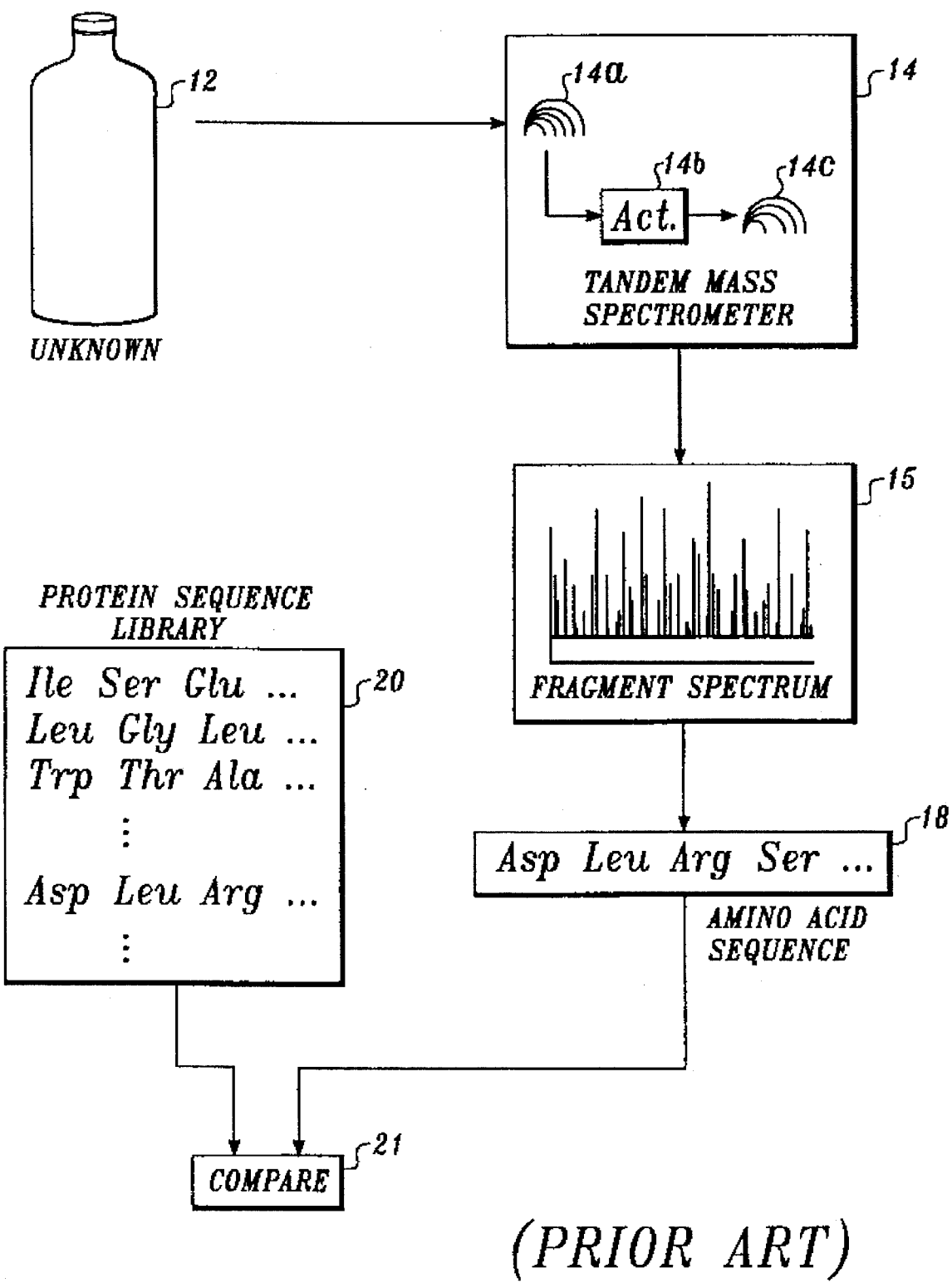
FIG. 1 is a block diagram depicting previous methods for correlating tandem mass spectrometer data with sequences from a protein sequence library.
Figure 5:
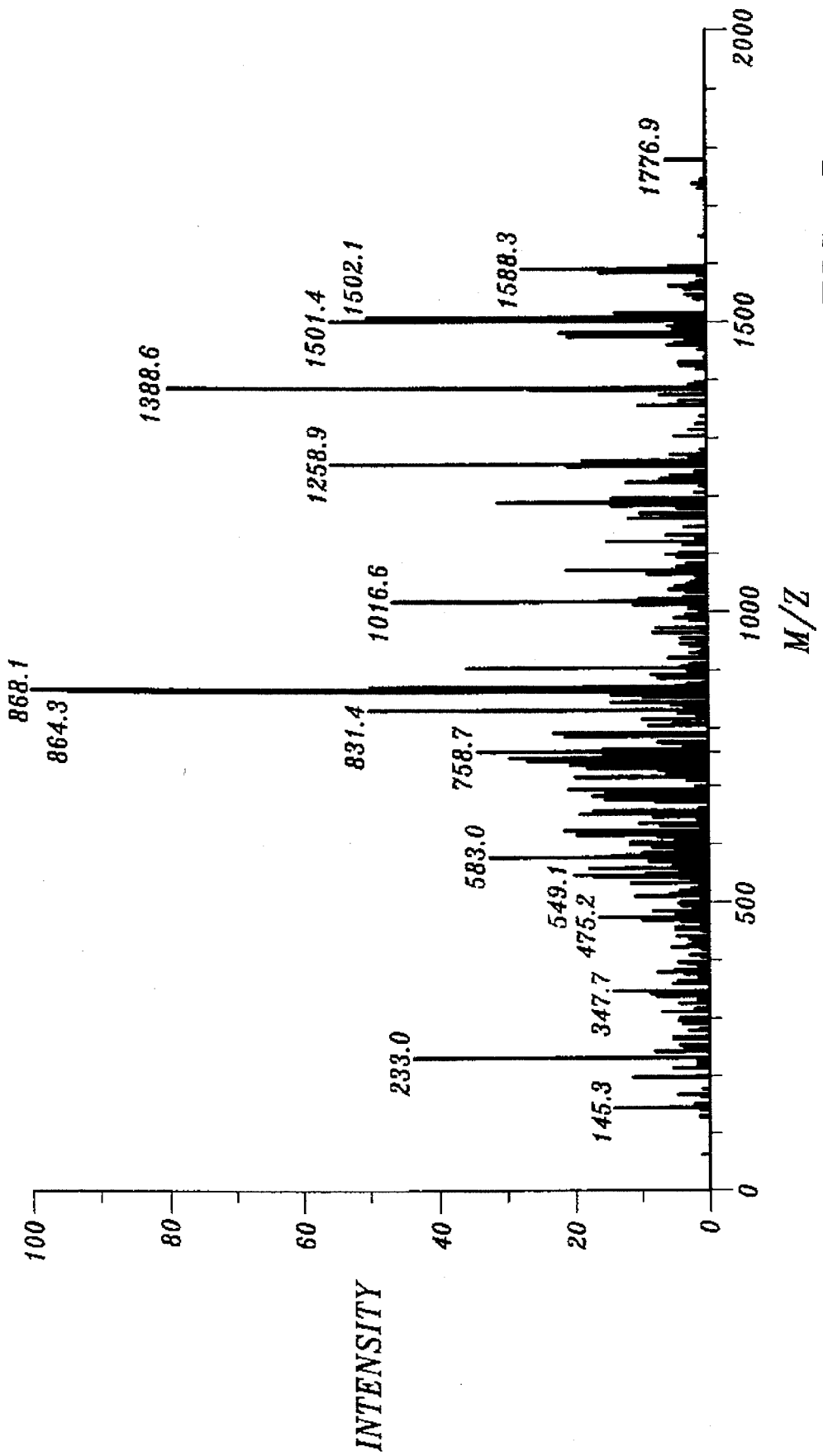
FIG. 5 is a fragment mass spectrum for a peptide of a type that can be used in connection with the present invention.
Figure 6A:
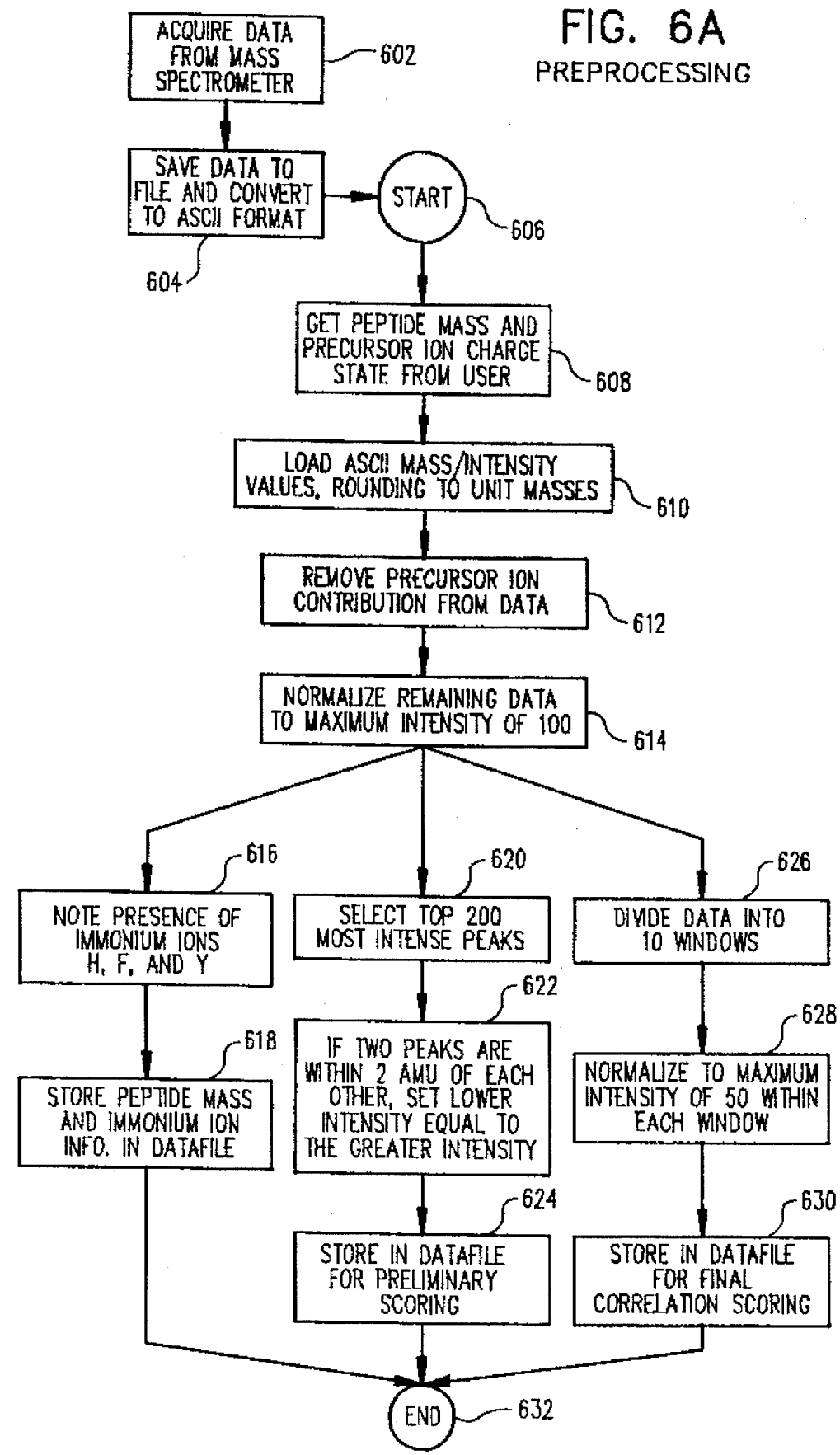
FIGS. 6A–6D are flow charts showing an analysis method, according to an embodiment of the present invention.
Figure 6B:
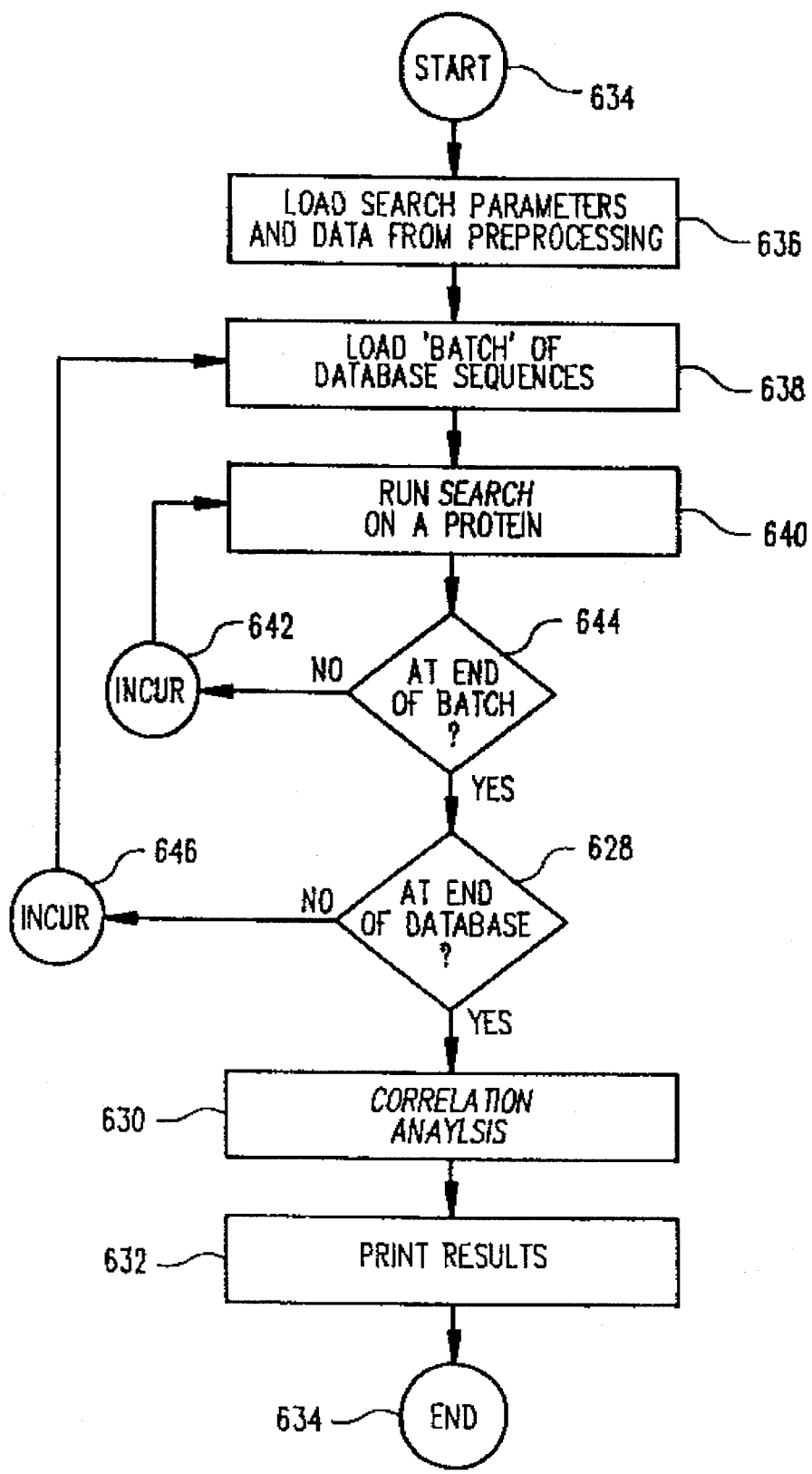
Figure 6C:
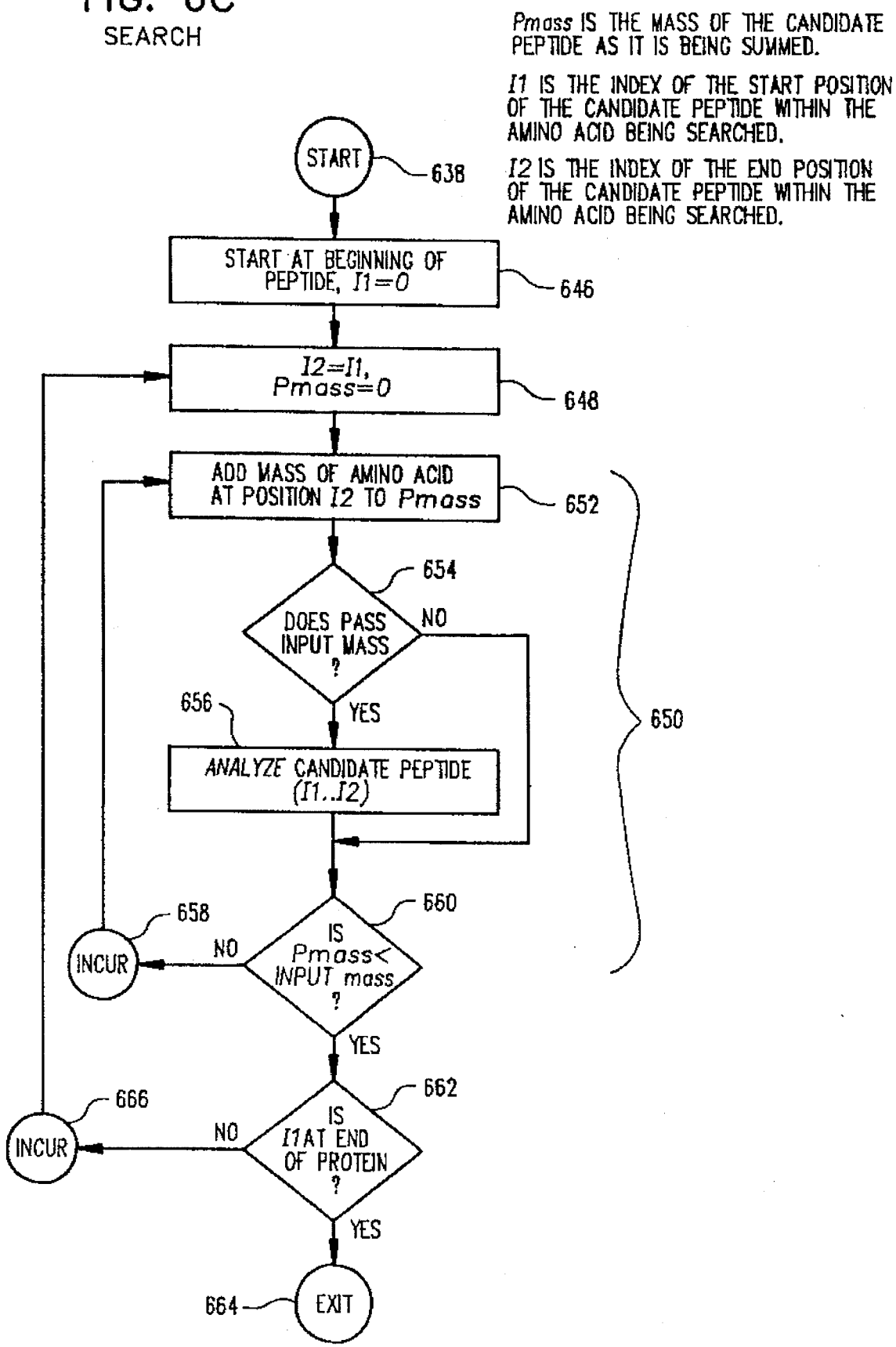
Figure 6D:
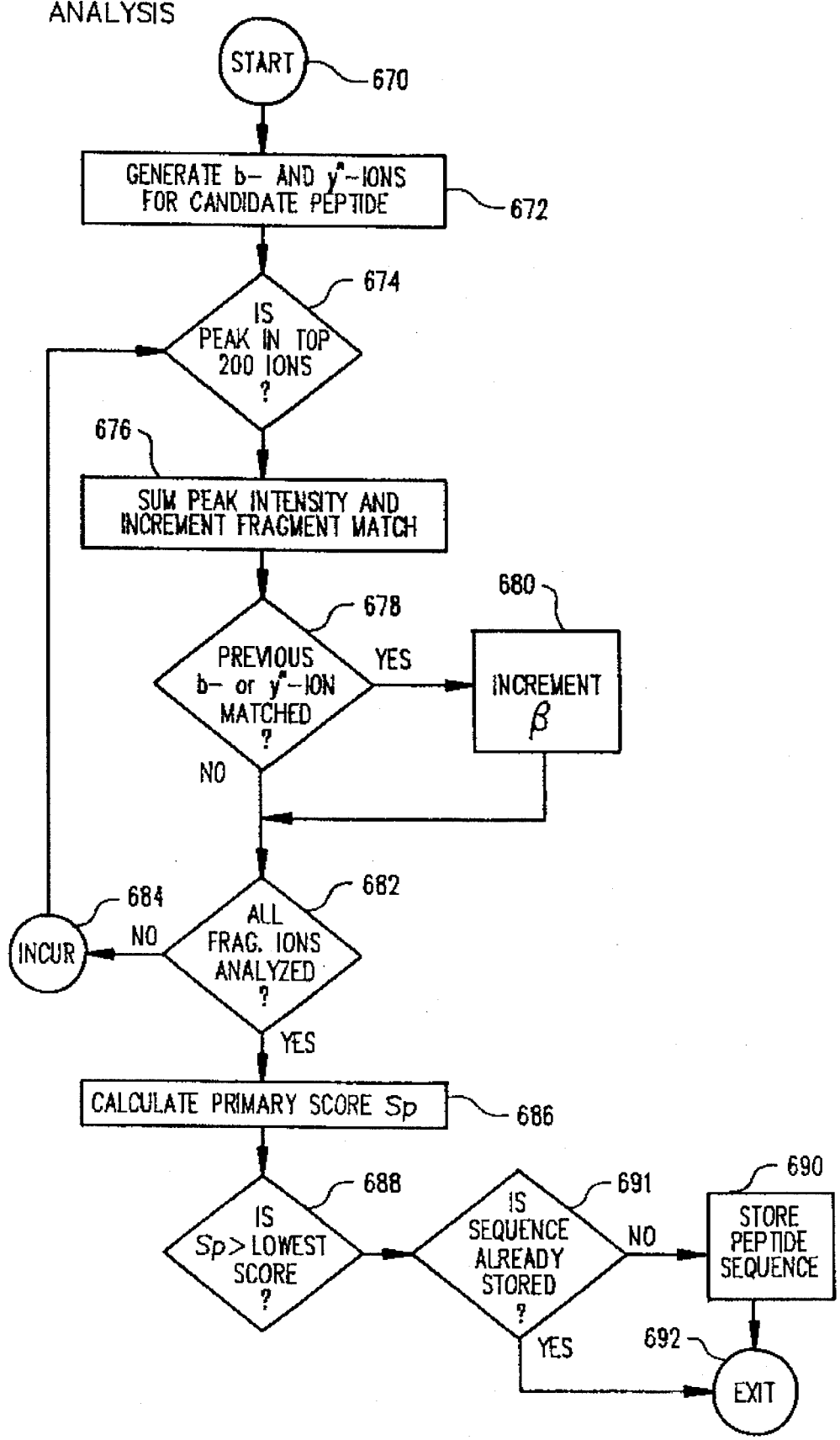
Figure 6E:
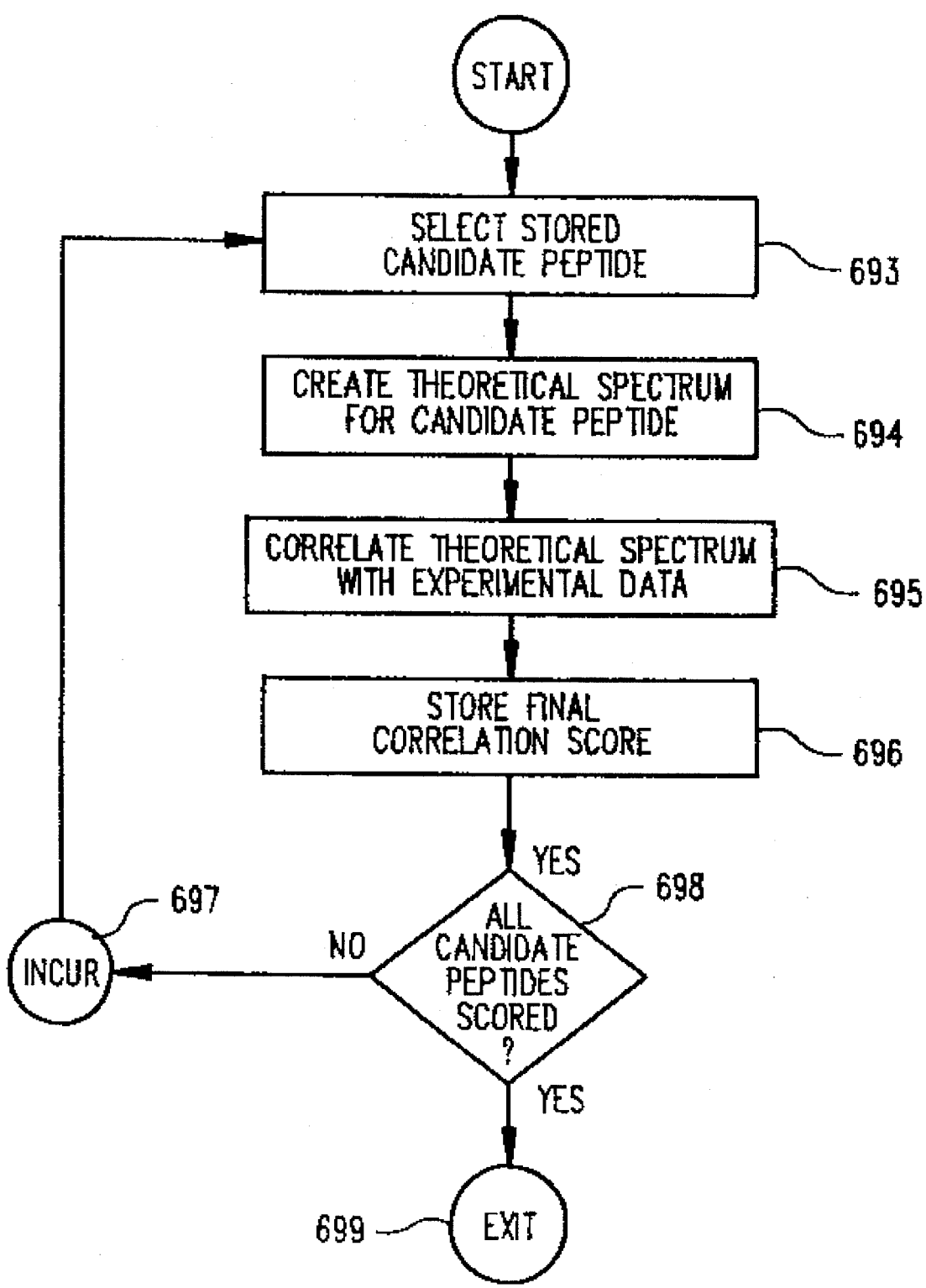

Before describing the embodiments of the present invention, it will be useful to describe, in greater detail, a previous method. As depicted in FIG. 1, the previous method is used for analysis of an unknown peptide 12. Typically the peptide will be output from a chromatography column which has been used to separate a partially fractionated protein. The protein can be fractionated by, for example, gel filtration chromatography and/or high performance liquid chromatography (HPLC). The sample 12 is introduced to a tandem mass spectrometer 14 through an ionization method such as electrospray ionization (ES). In the first mass spectrometer, a peptide ion is selected, so that a targeted component of a specific mass, is separated from the rest of the sample 14a. The targeted component is then activated or decomposed. In the case of a peptide, the result will be a mixture of the ionized parent peptide ("precursor ion") and component peptides of lower mass which are ionized to various states. A number of activation methods can be used including collisions with neutral gases (also referred to as collision induced dissolution). The parent peptide and its fragments are then provided to the second mass spectrometer 14c, which outputs an intensity and m/z for each of the plurality of fragments in the fragment mixture. This information can be output as a fragment mass spectrum 15. FIG. 5 provides an example of such a spectrum 15. In the spectrum 15 each fragment ion is represented as a bar graph whose abscissa value indicates the mass-to-charge ratio (m/z) and whose ordinate value represents intensity. According to previous methods, in order to correlate a fragment spectrum with sequences from a protein sequence library, a fragment sequence was converted into one or more amino acid sequences judged to correspond to the fragment spectrum. In one strategy, the weight of each of the amino acids is subtracted from the molecular weight of the parent ion to determine what might be the molecular weight of a fragment assuming, respectively, each amino acid is in the terminal position. It is determined if this fragment mass is found in the actual measured fragment spectrum. Scores are generated for each of the amino acids and the scores are sorted to generate a list of partial sequences for the next subtraction cycle. Cycles continue until subtraction of the mass of an amino acid leaves a difference of less than 0.5 and greater than −0.5. The result is one or more candidate amino acid sequences 18. This procedure can be automated as described, for example, in Yates III (1991) supra. One or more of the highest-scoring candidate sequences can then be compared 21 to sequences in a protein sequence library 20 to try to identify a protein having a sub-sequence similar or identical to the sequence believed to correspond to the peptide which generated the fragment spectrum 15.

Figure 2:
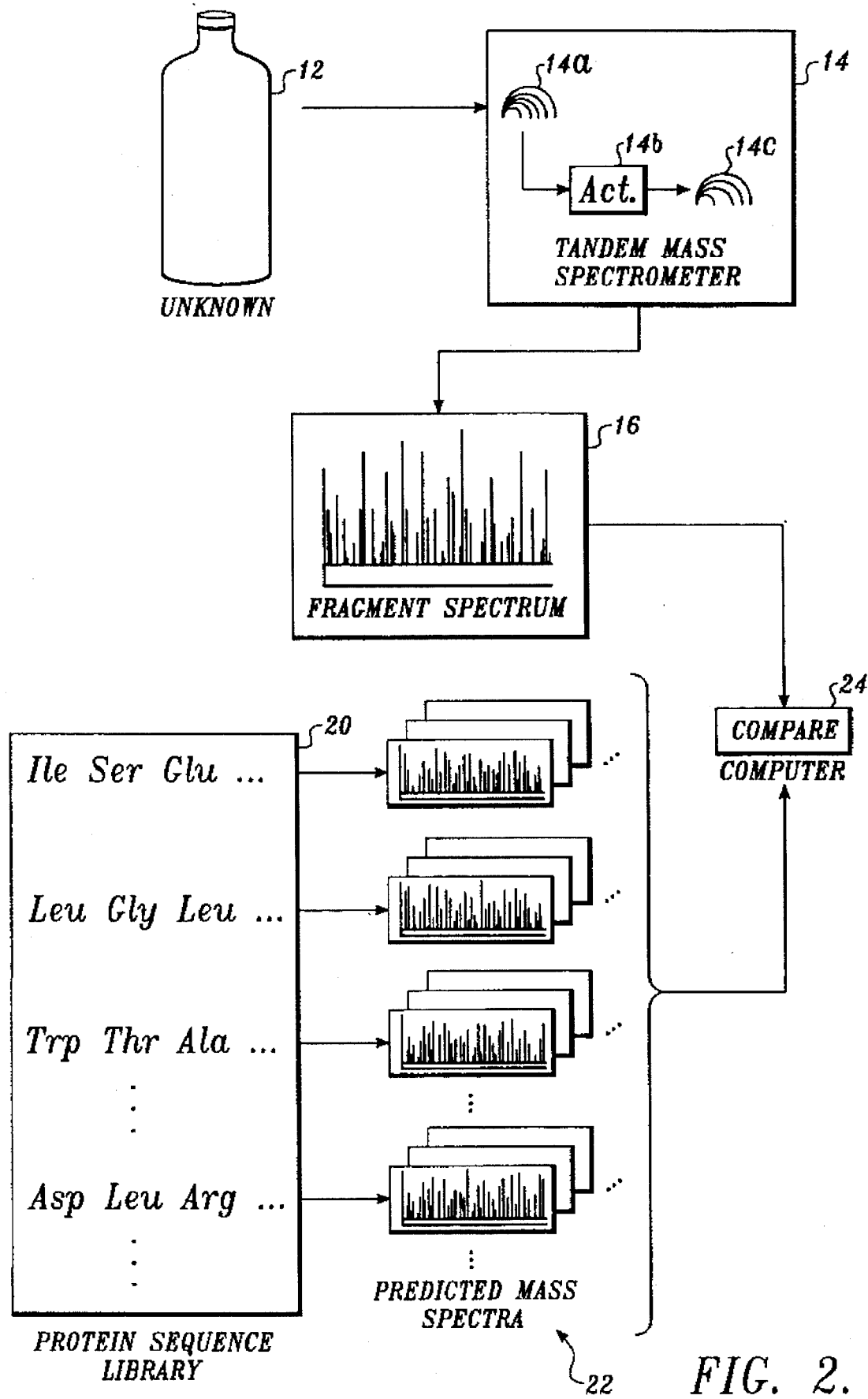
FIG. 2 is a block diagram showing a method for correlating tandem mass spectrometer data with sequences from a protein sequence library according to an embodiment of the present invention.

FIG. 2 shows an overview of a process according to the present invention. According to the process of FIG. 2, a fragment spectrum 16 is obtained in a manner similar to that described above for the fragment spectrum depicted in FIG. 1. Specifically, the sample 12 is provided to a tandem mass spectrometer 14. Procedures described below use a two-step process to acquire ms/ms data. However the present invention can also be used in connection with mass spectrometry approaches currently being developed which incorporate acquisition of ms/ms data with a single step. In one embodiment ms/ms spectra would be acquired at each mass. The first ms would separate the ions by mass-to-charge and the second would record the ms/ms spectrum. The second stage of ms/ms would acquire, e.g. 5 to 10 spectra at each mass transformed by the first ms.

A number of mass spectrometers can be used including a triple-quadruple mass spectrometer, a Fourier-transform cyclotron resonance mass spectrometer, a tandem time-of-flight mass spectrometer and a quadrupole ion trap mass spectrometer. In the process of FIG. 2, however, it is not necessary to use the fragment spectrum as a basis for hypothesizing one or more amino acid sequences. In the process of FIG. 2, sub-sequences contained in the protein sequence library 20 are used as a basis for predicting a plurality of mass spectra 22, e.g., using prediction techniques described more fully below.

A number of sequence libraries can be used, including, for example, the Genpept database, the GenBank database (described in Burks, et al., "GenBank: Current status and future directions in Methods in Enzymology", 183:3 (1990)), EMBL data library (described in Kahn, et al., "EMBL Data Library," *Methods in Enzymology*, 183:23 (1990)), the Protein Sequence Database (described in Barker, et al., "Protein Sequence Database," *Methods in Enzymology*, 1983:31 (1990), SWISS-PROT (described in Bairoch, et al., "The SWISS-PROT protein sequence data bank, recent developments," *Nucleic Acids Res.*, 21:3093–3096 (1993)), and PIR-International (described in "Index of the Protein Sequence Database of the International Association of Protein Sequence Databanks (PIR-International)" *Protein Seg Data Anal.* 5:67–192 (1993).

The predicted mass spectra 22 are compared 24 to the experimentally-derived fragment spectrum 16 to identify one or more of the predicted mass spectra which most closely match the experimentally-derived fragment spectrum 16. Preferably the comparison is done automatically by calculating a closeness-of-fit measure for each of the plurality of predicted mass spectra 22 (compared to the experimentally-derived fragment spectrum 16). It is believed that, in general, there is high probability that the peptide analyzed by the tandem mass spectrometer has an amino acid sequence identical to one of the sub-sequences taken from the protein sequence library 20 which resulted in a predicted mass spectrum 22 exhibiting a high closeness-of-fit with respect to the experimentally-derived fragment spectrum 16. Furthermore, when the peptide analyzed by the tandem mass spectrometer 14 was derived from a protein, it is believed there is a high probability that the parent protein is identical or similar to the protein whose sequence in the protein sequence library 20 includes a sub-sequence that resulted in a predicted mass spectra 22 which had a high closeness-of-fit with respect to the fragment spectrum 16. Preferably, the entire procedure can be performed automatically using, e.g, a computer to calculate predicted mass spectra 22 and/or to perform comparison 24 of the predicted mass spectra 22 with the experimentally-derived fragment spectrum 16.

Figure 3:
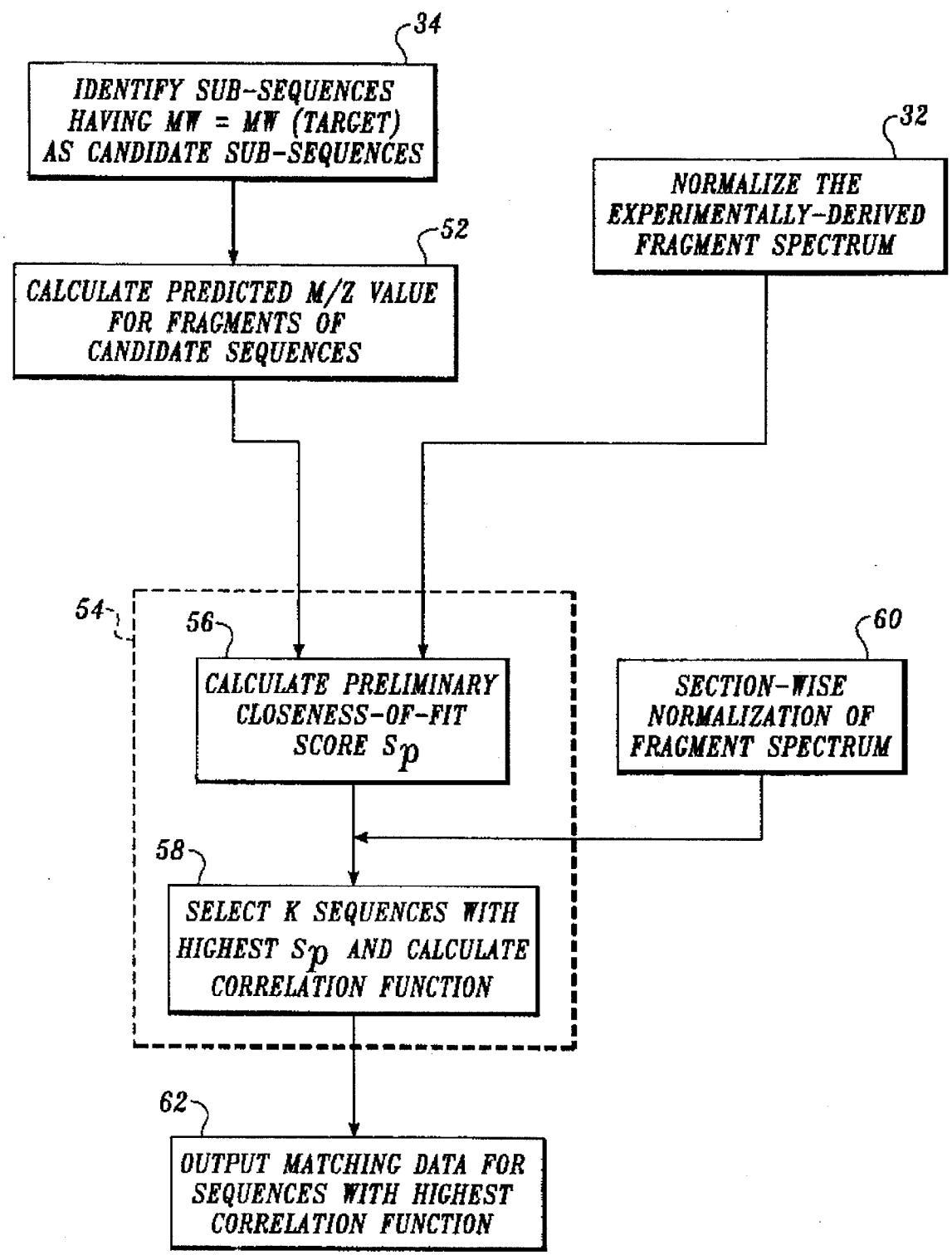
FIG. 3 is a flow chart showing steps for correlating tandem mass spectrometry data with amino acid sequences, according to an embodiment of the present invention.

FIG. 3 is a flow diagram showing one method for predicting mass spectra 22 and performing the comparison 24. According to the method of FIG. 3, the experimentally-derived fragment spectrum 16 is first normalized 32. According to one normalization method, the experimentally-derived fragment spectrum 16 is converted to a list of masses and intensities. The values for the precursor ion are removed from the file. The square root of all the intensity values is calculated and normalized to a maximum intensity of 100. The 200 most intense ions are divided into ten mass regions and the maximum intensity is normalized to 100 within each region. Each ion which is within 3.0 daltons of its neighbor on either side is given the greater intensity value, if a neighboring intensity is greater than its own intensity. Of course, other normalizing methods can be used and it is possible to perform analysis without performing normalization, although normalization is, in general, preferred. For example, it is possible to use maximum intensities with a value greater than or less than 100. It is possible to select more or fewer than the 200 most intense ions. It is possible to divide into more or fewer than 10 mass regions. It is possible to make the window for assuming the neighboring intensity value to be greater than or less than 3.0 daltons.

In order to generate predicted mass spectra from a protein sequence library, according to the process of FIG. 3, sub-sequences within each protein sequence are identified which have a mass which is within a tolerance amount of the mass of the unknown peptide. As noted above, the mass of the unknown peptide is known from the tandem mass spectrometer 34. Identification of candidate sub-sequences 34 is shown in greater detail in FIG. 4. In general, the process of identifying candidate sub-sequences involves summing the masses of linear amino acid sequences until the sum is either within a tolerance of the mass of the unknown peptide (the "target" mass) or has exceeded the target mass (plus tolerance). If the mass of the sequence is within tolerance of the target mass, the sequence is marked as a candidate. If the mass of the linear sequence exceeds the mass of the unknown peptide, then the algorithm is repeated, beginning with the next amino acid position in the sequence.

Figure 4:
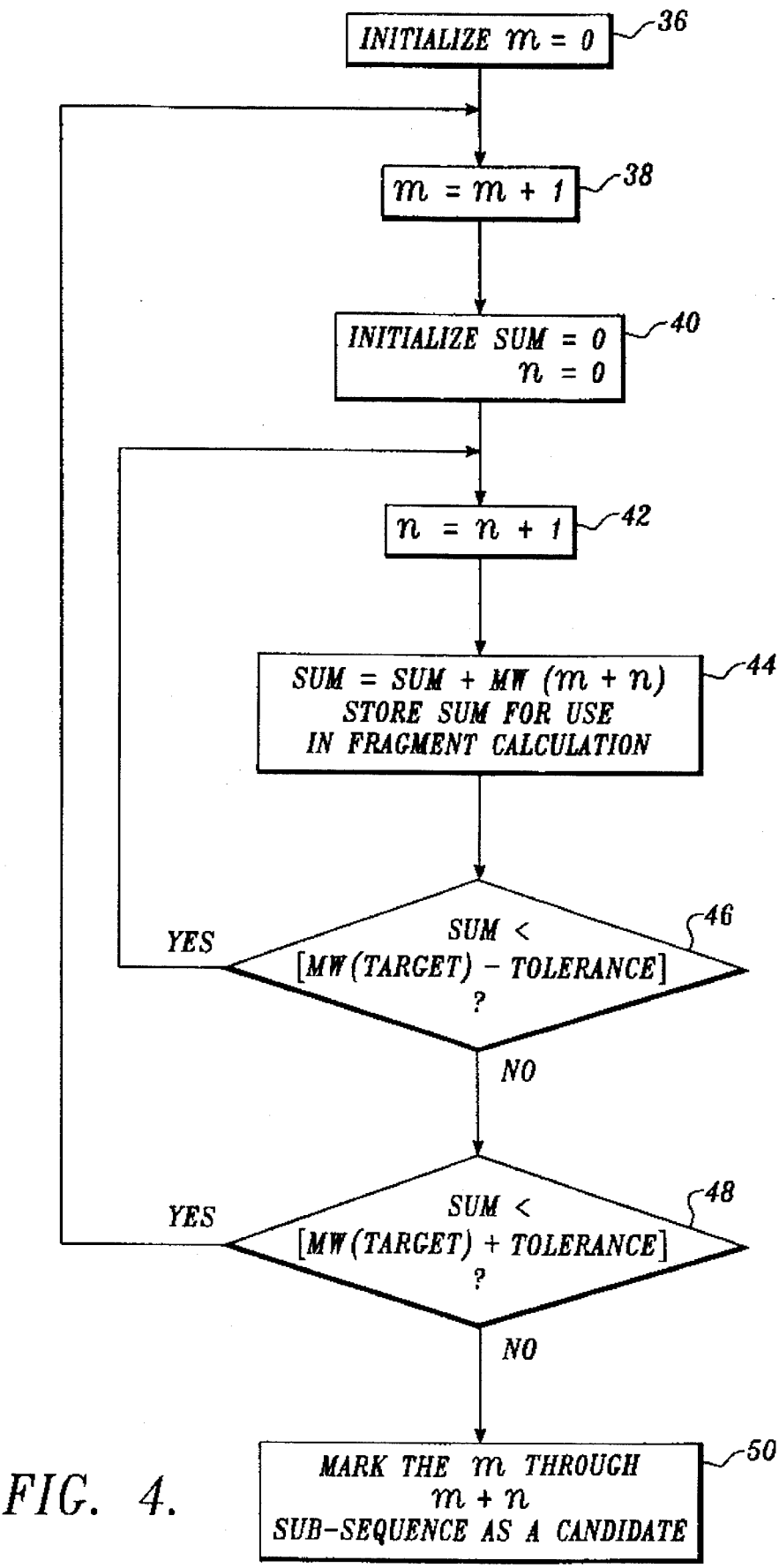
FIG. 4 is a flow diagram showing details of a method for the step of identifying candidate sub-sequences of FIG. 3.

According to the method of FIG. 4, a variable m, indicating the starting amino acid along the sequence is initialized to 0 and incremented by 1 (36, 38). The sum, representing the cumulative mass and a variable n representing the number of amino acids thus far calculated in the sum, are initially set to 0 (40) and variable n is incremented 42. The molecular weight of a peptide corresponding to a subsequence of a protein sequence is calculated in iterative fashion by steps 44 and 46. In each iteration, the sum is incremented by the molecular weight of the amino acid of the next (nth) amino acid in the sequence 44. Values of the sum 44 may be stored for use in calculating fragment masses for use in predicting a fragment mass spectrum as described below. If the resulting sum is less than the target mass decremented by a tolerance 46, the value of n is incremented 42 and the process is repeated 44. A number of tolerance values can be used. In one embodiment, a tolerance value of ±0.05% of the mass of the unknown peptide was used. If the new sum is no longer less than a tolerance amount below the target mass, it is then determined if the new sum is greater than the target mass plus the tolerance amount. If the new sum is more than the tolerance amount in excess of the target mass, this particular sequence is not considered a candidate sequence and the process begins again, starting from a new starting point in the sequence (by incrementing the starting point value m (38)). If, however, the sum is not greater than the target mass plus the tolerance amount, it is known that the sum is within one tolerance amount of a target mass and, thus, that the sub-sequence beginning with mth amino and extending to the (m+n)th amino acid of the sequence is a candidate sequence. The candidate sequence is marked, e.g., by storing the values of m and n to define this sub-sequence.

Returning to FIG. 3, once a plurality of candidate subsequences have been identified, a fragment mass spectrum is predicted for each of the candidate sequences 52. The fragment mass spectrum is predicted by calculating the fragment ion masses for the type b- and y- ions for the amino acid sequence. When a peptide is fragmented and the charge is retained on the N-terminal cleavage fragment, the resulting ion is labelled as a b-type ion. If the charge is retained on the c-type terminal fragment, it is labelled a y-type ion. Masses for type b- ions were calculated by summing the amino acid masses and adding the mass of a proton. Type y-ions were calculated by summing, from the c-terminus, the masses of the amino acids and adding the mass of water and a proton to the initial amino acid. In this way, it is possible to calculate an m/z for each fragment. However, in order to provide a predicted mass spectrum, it is also necessary to assign an intensity value for each fragment. It might be possible to predict, on a theoretical basis, intensity value for each fragment. However, this procedure is difficult. It has been found useful to assign intensities in the following fashion. The value of 50.0 is assigned to each b and y ion. To masses of 1 dalton on either side of the fragment ion, an intensity of 25.0 is assigned. Peak intensities of 10.0 and −17.0 and −18.0 daltons below the m/z of each b- and y- ion location (for both $NH_3$ and $H_2O$ loss), and peak intensities of 10.0 and −28.0 amu of each type b ion location (for type a- ions).

Returning to FIG. 3, after calculation of predicted m/z values and assignment of intensities, it is preferred to calculate a measure of closeness-of-fit between the predicted mass spectra 22 and the experimentally-derived fragment spectrum 16. A number of methods for calculating closeness-of-fit are available. In the embodiment depicted in FIG. 3, a two-step method is used 54. The two-step method includes calculating a preliminary closeness-of-fit score, referred to here as $S_p$ 56 and, for the highest-scoring amino acid sequences, calculating a correlation function 58.

According to one embodiment, $S_p$ is calculated using the following formula:

$$S_p = (\Sigma i_m) * n_i * (1+\beta) * (1-\rho)/n_\tau \qquad (1)$$

where $i_m$=matched intensities, $n_i$=number of matched fragment ions, $\beta$=type b- and y-ion continuity, $\rho$=presence of immonium ions and their respective amino acids in the predicted sequence, $n_\tau$=total number of fragment ions. The factor, $\beta$, evaluates the continuity of a fragment ion series. If there was a fragment ion match for the ion immediately preceding the current type b- or y-ion, $\beta$ is incremented by 0.075 (from an initial value of 0.0). This increases the preliminary score for those peptides matching a successive series of type b- and y-ions since extended series of ions of the same type are often observed in MS/MS spectra. The factor $\rho$ evaluates the presence of immonium ions in the low mass end of the mass spectrum. Immonium ions are diagnostic for the presence of some types of amino acids in the sequence. If immonium ions are present at 110.0, 120.0, or 136.0 Da (±1.0 Da) in the processed data file of the unknown peptide with normalized intensities greater than 40.0, indicating the presence of histidine, phenylalanine, and tyrosine respectively, then the sequence under evaluation is checked for the presence of the amino acid indicated by the immonium ion. The preliminary score, $S_p$, for the peptide is either augmented or depreciated by a factor of $(1-\rho)$ where $\rho$ is the sum of the penalties for each of the three amino acids whose presence is indicated in the low mass region. Each individual $\rho$ can take on the value of −0.15 if there is a corresponding low mass peak and the amino acid is not present in the sequence, +0.15 if there is a corresponding low mass peak and the amino acid is present in the sequence, or 0.0 if the low mass peak is not present. The total penalty can range from −0.45 (all three low mass peaks present in the spectrum yet none of the three amino acids are in the sequence) to +0.45 (all three low mass peaks are present in the spectrum and all three amino acids are in the sequence).

Following the calculation of the preliminary closeness-of-fit score $S_p$, those candidate predicted mass spectra having the highest $S_p$ scores are selected for further analysis using the correlation function 58. The number of candidate predicted mass spectra which are selected for further analysis will depend largely on the computational resources and time available. In one embodiment, 300 candidate peptide sequences with the highest preliminary score were selected.

For purposes of calculating the correlation function, 58, the experimentally-derived fragment spectrum is preprocessed in a fashion somewhat different from preprocessing 32 employed before calculating $S_p$. For purposes of the correlation function, the precursor ion was removed from the spectrum and the spectrum divided into 10 sections. Ions in each section were then normalized to 50.0. The sectionwise normalized spectra 60 were then used for calculating the correlation function. According to one embodiment, the discrete correlation between the two functions is calculated as:

$$R_\tau = \sum_{i=0}^{n-1} x_i y_{i+\tau} \qquad (2)$$

where $\tau$ is a lag value. The discrete correlation theorem states that the discrete correlation of two real functions x and y is one member of the discrete Fourier transform pair $$R_\tau \Leftrightarrow X_\tau Y^*_\tau \qquad (3)$$

where X(t) and Y(t) are the discrete Fourier transforms of x(i) and y(i) and the $Y^*$ denotes complex conjugation.

Therefore, the cross-correlations can be computed by Fourier transformation of the two data sets using the fast Fourier transform (FFT) algorithm, multiplication of one transform by the complex conjugate of the other, and inverse transformation of the resulting product. In one embodiment, all of the predicted spectra as well as the pre-processed unknown spectrum were zero-padded to 4096 data points since the MS/MS spectra are not periodic (as intended by the correlation theorem) and the FFT algorithm requires N to be an integer power of two, so the resulting end effects need to be considered. The final score attributed to each candidate peptide sequence is R(0) minus the mean of the cross-correlation function over the range $-75 < t < 75$. This modified "correlation parameter" described in Powell and Heiftje, *Anal. Chim. Acta*, Vol. 100, pp 313–327 (1978) shows better discrimination over just the spectral correlation coefficient R(0). The raw scores are normalized to 1.0. In one embodiment, output 62 includes the normalized raw score, the candidate peptide mass, the unnormalized correlation coefficient, the preliminary score, the fragment ion continuity $\beta$, the immonium ion factor $\tau$, the number of type b- and y-ions matched out of the total number of fragment ions, their matched intensities, the protein accession number, and the candidate peptide sequence.

If desired, the correlation function 58 can be used to automatically select one of the predicted mass spectra 22 as corresponding to the experimentally-derived fragment spectrum 16. Preferably, however, a number of sequences from the library 20 are output and final selection of a single sequence is done by a skilled operator.

In addition to predicting mass spectra from protein sequence libraries, the present invention also includes predicting mass spectra based on nucleotide databases. The procedure involves the same algorithmic approach of cycling through the nucleotide sequence. The 3-base codons will be converted to a protein sequence and the mass of the amino acids summed in a fashion similar to the summing depicted in FIG. 4. To cycle through the nucleotide sequence, a 1-base increment will be used for each cycle. This will allow the determination of an amino acid sequence for each of the three reading frames in one pass. The scoring and reporting procedures for the search can be the same as that described above for the protein sequence database.

Depending on the computing and time resources available, it may be advantageous to employ data-reduction techniques. Preferably these techniques will emphasize the most informative ions in the spectrum while not unduly affecting search speed. One technique involves considering only some of the fragment ions in the MS/MS spectrum. A spectrum for a peptide may contain as many as 3,000 fragment ions. According to one data reduction strategy, the ions are ranked by intensity and some fraction of the most intense ions (e.g., the top 200 most intense ions) will be used for comparison. Another approach involves subdividing the spectrum into, e.g., 4 or 5 regions and using the 50 most intense ions in each region as part of the data set. Yet another approach involves selecting ions based on the probability of those ions being sequence ions. For example, ions could be selected which exist in mass windows of 57 through 186 daltons (range of mass increments for the 20 common amino acids from GLY to TRP) that contain diagnostic features of type b- or y- ions, such as losses of 17 or 18 daltons ($NH_3$ or $H_2O$) or a loss of 28 daltons (CO).

The techniques described above are, in general, applicable to spectra of peptides with charged states of +1 or +2, typically having a relatively short amino acid sequence. Using a longer amino acid sequence increases the probability of a unique match to a protein sequence. However, longer peptide sequences have a greater likelihood of containing more basic amino acids, and thus producing ions of higher charge state under electro-spray ionization conditions. According to one embodiment of the invention, algorithms are provided for searching a database with MS/MS spectra of highly charged peptides (+3, +4, +5, etc.). According to one approach, the search program will include an input for the charge state (N) of the precursor ion used in the MS/MS analysis. Predicted fragment ions will be generated for each charge state less than N. Thus, for peptide of +4, the charge states of +1, +2 and +3 will be generated for each fragment ion and compared to the MS/MS spectrum.

The second strategy for use with multiply charged spectra is the use of mathematical deconvolution to convert the multiply charged fragment ions to their singly charged masses. The deconvoluted spectrum will then contain the fragment ions for the multiply charged fragment ions and their singly charged counterparts.

To speed up searches of the database, a directed-search approach can be used. In cases where experiments are performed on specific organisms or specific types of proteins, it is not necessary to search the entire database on the first pass. Instead, a search sequence protein specific to a species or a class of proteins can be performed first. If the search does not provide reasonable answers, then the entire database is searched.

A number of different scoring algorithms can be used for determining preliminary closeness of fit or correlation. In addition to scoring based on the number of matched ions multiplied by the sum of the intensity, scoring can be based on the percentage of continuous sequence coverage represented by the sequence ions in the spectrum. For example, a 10 residue peptide will potentially contain 9 each of b- and y-type sequence ions. If a set of ions extends from $B_1$ to $B_9$, then a score of 100 is awarded, but if a discontinuity is observed in the middle of the sequence, such as missing the $B_5$ ion, a penalty is assessed. The maximum score is awarded for an amino acid sequence that contains a continuous ion series in both the b and y directions.

In the event the described scoring procedures do not delineate an answer, an additional technique for spectral comparison can be used in which the database is initially searched with a molecular weight value and a reduced set of fragment ions. Initial filtering of the database occurs by matching sequence ions and generating a score with one of the methods described above. The resulting set of answers will then undergo a more rigorous inspection process using a modified full MS/MS spectrum. For the second stage analysis, one of several spectral matching approaches developed for spectral library searching is used. This will require generating a "library spectrum" for the peptide sequence based on the sequence ions predicted for that amino acid sequence. Intensity values for sequence ions of the "library spectrum" will be obtained from the experimental spectrum. If a fragment ion is predicted at m/z 256, then the intensity value for the ion in the experimental spectrum at m/z=256 will be used as the intensity of the ion in the predicted spectrum. Thus, if the predicted spectrum is identical to the "unknown" spectrum, it will represent an ideal spectrum. The spectra will then be compared using a correlation function. In general, it is believed that the majority of computational time for the above procedure is spent in the iterative search process. By multiplexing the analysis of multiple MS/MS spectra in one pass through the database, an overall improvement in efficiency will be realized. In addition, the mass tolerance used in the initial pre-filtering can affect search times by increasing or decreasing the number of sequences to analyze in subsequent steps. Another approach to speed up searches involves a binary encryption scheme where the mass spectrum is encoded as peak/no peak at every mass depending on whether the peak is above a certain threshold value. If intensive use of a protein sequence library is contemplated, it may be possible to calculate and store predicted mass values of all subsequences within a predetermined range of masses so that at least some of the analysis can be performed by table look-up rather than calculation.

FIGS. 6A–6E are flow charts showing an analysis procedure according to one embodiment of the present invention. After data is acquired from the tandem mass spectrometer, as described above 602, the data is saved to a file and converted to an ASCII format 604. At this point, a preprocessing procedure is started 606. The user enters information regarding the peptide mass in the precursor ion charge state 608. Mass/intensity values are loaded from the ASCII file, with the values being rounded to unit masses 610. The previously-identified precursor ion contribution of this data is removed 612. The remaining data is normalized to a maximum intensity of 100 614. At this point, different paths can be taken. In one case, the presence of any immonium ions (H, F and Y) is noted 616 and the peptide mass and immonium ion information is stored in a datafile 618. In another route, the 200 most intense peaks are selected 620. If two peaks are within a predetermined distance (e.g., 2 amu) of each other, the lower intensity peak is set equal to a greater intensity 622. After this procedure, the data is stored in a datafile for preliminary scoring 624. In another route, the data is divided into a number of windows, for example ten windows 626. Normalization is performed within each window, for example, normalizing to a maximum intensity of 50 628. This data is then stored in a datafile for final correlation scoring 630. This ends the preprocessing phase, according to this embodiment 632.

The database search is started 634 and the search parameters and the data obtained from the preprocessing procedure (FIG. 6A) are loaded 636. A first batch of database sequences is loaded 638 and a search procedure is run on a particular protein 640. The search procedure is detailed in FIG. 6C. As long as the end of the batch has not been reached the index is incremented 642 and the search routine is repeated 640. Once it is determined that the end of a batch has been reached 644, as long as the end of the database has not been reached, the second index 646 is incremented and a new batch of database sequences is loaded 638. Once the end of the database has been reached 628, a correlation analysis is performed 630 (as detailed in FIG. 6E), the results are printed 632 and the procedure ends 634.

When the search procedure is started 638 (FIG. 6C), an index I1 is set to zero 646 to indicate the start position of the candidate peptide within the amino acid being searched 640. A second index I2, indicating the end position of the candidate peptide within the amino acid being searched, is initially set equal to I1 and the variable Pmass, indicating the accumulated mass of the candidate peptide is initialized to zero 648. During each iteration through a given candidate peptide 650 the mass of the amino acid at position I2 is added to Pmass 652. It is next determined whether the mass thus-far accumulated (Pmass) equals the input mass (i.e., the mass of the peptide) 654. In some embodiments, this test may be performed as plus or minus a tolerance rather than requiring strict equality, as noted above. If there is equality (optionally within a tolerance) an analysis routine is started 656 (detailed in FIG. 6D). Otherwise, it is determined whether Pmass is less than the input mass (optionally within a tolerance). If not, the index I2 is incremented 658 and the mass of the amino acid at the next position (the incremented I2 position) is added to Pmass 652. If Pmass is greater than the input mass (optionally by more than a tolerance 660) it is determined whether index I1 is at the end of a protein 662. If so, the search routine exits 664. Otherwise, index I1 is incremented 666 so that the routine can start with a new start position of a candidate peptide and the search procedure returns to block 648.

When the analysis procedure is started 670 (FIG. 6D), data indicative of b- and y- ions for the candidate peptide are generated 672, as described above. It is determined whether the peak is within the top 200 ions 674. The peak intensity is summed and the fragmented match index is incremented 676. If previous b- or y- ions are matched 678, the β index is incremented 680. Otherwise, it is determined whether all fragment ions have been analyzed. If not, the fragment index is incremented 684 and the procedure returns to block 674. Otherwise, a preliminary score such as $S_p$, described above is calculated 686. If the newly-calculated $S_p$ is greater than the lowest score 688 the peptide sequence is stored 690 unless the sequence has already been stored, in which case the procedure exits 692.

At the beginning of the correlation analysis (FIG. 6E), a stored candidate peptide is selected 693. A theoretical spectrum for the candidate peptide is created 694, correlated with experimental data 695 and a final correlation score is obtained 696, as described above. The index is incremented 697 and the process repeated from block 693 unless all candidate peptides have been scored 698, in which case the correlation analysis procedure exits 699.

The following examples are offered by way of illustration, not limitation.

EXPERIMENTAL EXAMPLE #1

MHC complexes were isolated from HS-EBV cells transformed with HLA-DRB*0401 using antibody affinity chromatography. Bound peptides were released and isolated by filtration through a Centricon 10 spin column. The heavy chain of glycosaparginase from human leukocytes was isolated. Proteolytic digestions were performed by dissolving the protein in 50 mM ammonium bicarbonate containing 10 mM $Ca^{++}$, pH 8.6. Trypsin was added in a ratio of 100/1 protein/enzyme.

Analysis of the resulting peptide mixtures was performed by LC-MS and LC-MS/MS. Briefly, molecular weights of peptides were recorded by scanning Q3 or Q1 at a rate of 400 Da/sec over a mass range of 300 to 1600 throughout the HPLC gradient. Sequence analysis of peptides was performed during a second HPLC analysis by selecting the precursor ion with a 6 amu (FWHH) wide window in $Q_1$ and passing the ions into a collision cell filled with argon to a pressure of 3–5 mtorr. Collision energies were on the order of 20 to 50 eV. The fragment ions produced in $Q_2$ were transmitted to $Q_3$ and a mass range of 50 Da to the molecular weight of the precursor ion was scanned at 500 Da/sec to record the fragment ions. The low energy spectra of 36 peptides were recorded and stored on disk. The genpept database contains protein sequences translated from nucleotide sequences. A text search of the database was performed to determine if the sequences for the peptide amino acid sequences used in the analysis were present in the database. Subsequently, a second database was created from the whole database by appending amino acid sequences for peptides not included.

The spectrum data was converted to a list of masses and intensities and the values for the precursor ion were removed from the file. The square root of all the intensity values was calculated and normalized to a maximum intensity of 100.0. All ions except the 200 most intense ions were removed from the file. The remaining ions were divided into 10 mass regions and the maximum intensity normalized to 100.0 within each region. Each ion within 3.0 daltons of its neighbor on either side was given the greater intensity value, if the neighboring intensity was greater than its own intensity. This processed data was stored for comparison to the candidate sequences chosen from the database search. The MS/MS spectrum was modified in a different manner for calculation of a correlation function. The precursor ion was removed from the spectrum and the spectrum divided into 10 equal sections. Ions in each section were then normalized to 50.0. This spectrum was used to calculate the correlation coefficient against a predicted MS/MS spectrum for each amino acid sequence retrieved from the database.

Amino acid sequences from each protein were generated by summing the masses, using average masses for the amino acids, of the linear amino acid sequence from the amino terminus (n). If the mass of the linear sequence exceeded the mass of the unknown peptide, then the algorithm returned to the amino terminal amino acid and began summing amino acid masses from the n+1 position. This process was repeated until every linear amino acid sequence combination had been evaluated. When the mass of the amino acid sequence was within ±0.05% (minimum of ±1 Da) of the mass of the unknown peptide, the predicted m/z values for the type b- and y-ions were generated and compared to the fragment ions of the unknown sequence. A preliminary score ($S_p$) was generated and the top 300 candidate peptide sequences with the highest preliminary score were ranked and stored. A final analysis of the top 300 candidate amino acid sequences was performed with a correlation function. Using this function a theoretical MS/MS spectrum for the candidate sequence was compared to the modified experimental MS/MS spectrum. Correlation coefficients were calculated, ranked and reported. The final results were ranked on the basis of the normalized correlation coefficient.

The spectrum shown in FIG. 5 was obtained by LC-MS/MS analysis of a peptide bound to a DRB*0401 MHC class II complex. A search of the genpept database containing 74,938 protein sequences identified 384,398 peptides within a mass tolerance of ±0.05% (minimum of ±1Da) of the molecular weight of this peptide. By comparing fragment ion patterns predicted for each of these amino acid sequences to the pre-processed MS/MS spectra and calculating a preliminary score, the number of candidate sequences was cutoff at 300. A correlation analysis was then performed with the predicted MS/MS spectra for each of these sequences and the modified experimental MS/MS spectrum. The results of the search through the genpept database with the spectrum in FIG. 5 are displayed in Table 1. Two peptides of similar sequence, DLRSWTAADAAQISK [Seq. ID No. 1], DLRSWTAADAAQISQ [Seq. ID No. 2], were identified as the highest scoring sequences ($C_n$ values). Their correlation coefficients are identical so their rankings in Table 1 are arbitrary. The amino acid sequence DLRSWTAADAAQISK [Seq. ID No. 1] occurs in five proteins in the genpept database while the sequence DLRSWTAADAAQISQ [Seq. ID No. 2] occurs in only one. The top three sequences appear in immunologically related proteins and the rest of the proteins appear to have no correlation to one another. A second search using the same MS/MS spectrum was performed with the *Homo sapiens* subset of the genpept database to compare the results. These data are presented in Table 2. In both searches the correct sequence tied for the top position. Both amino acid sequences have identical correlation coefficients, $C_n$, although the sequences differ by Lys and Gln at the C-terminus. These two amino acids have the same nominal mass and would be expected to produce similar MS/MS spectra. The sum of the normalized fragment ion intensities, $I_m$, for the matched fragment ions for the two peptides are different with the correct sequence having the greater value. The correct sequence also matched an additional fragment ion in the preliminary scoring procedure identifying 70% of the predicted fragment ions for this amino acid sequence in the pre-processed spectrum. These matches are determined as part of the preliminary scoring procedure.

TABLE 1

| No | Mass | $C_n$ | C | $S_p$ | β | ρ | Ions | $I_m$ | Accession No | No of Proteins | Sequence |
|---|---|---|---|---|---|---|---|---|---|---|---|
| 1 | 1734.90 | 1.000 | 4.203 | 1809.9 | 1.125 | 0.000 | 20/30 | 1277.61 | X17273 | +5 | DLRSWTAADTAAQISK |
| 2 | 1734.86 | 1.000 | 4.203 | 2020.1 | 1.200 | 0.000 | 21/30 | 1311.79 | M84380 | | DLRSWTAADTAAQISQ |
| 3 | 1733.91 | 0.893 | 3.752 | 1440.8 | 0.975 | 0.000 | 19/30 | 1151.87 | X60251 | +2 | DLRSWTAADTAAQVTQ |
| 4 | 1733.96 | 0.727 | 3.057 | 606.1 | 0.525 | 0.000 | 14/30 | 851.71 | m90516 | | VIFLEDDDVAAVVDGR |
| 5 | 1733.96 | 0.685 | 2.881 | 1012.5 | 0.750 | 0.000 | 16/28 | 1012.47 | D13262 | +1 | TDMEELLAGIWQDVL |
| 6 | 1734.94 | 0.684 | 2.874 | 805.8 | 0.675 | 0.000 | 16/32 | 962.12 | S58174 | | RCLTASTLGLTGNVNVN |
| 7 | 1743.96 | 0.683 | 2.869 | 763.4 | 0.600 | 0.000 | 15/30 | 954.28 | X17149 | | GSSLMAEDNLELAVRK |
| 8 | 1733.97 | 0.767 | 2.839 | 790.1 | 0.675 | 0.000 | 17/36 | 998.90 | M19085 | | SGILTLSGGLSSNAEVTAG |
| 9 | 1733.93 | 0.675 | 2.836 | 682.9 | 0.525 | 0.000 | 13/26 | 895.55 | M29146 | +1 | YPSKQINELWENVL |
| 10 | 1734.90 | 0.668 | 2.809 | 590.8 | 0.525 | 0.000 | 15/36 | 929.73 | M84615 | | AKSGEANVTSATGTIGGTI |
| 11 | 1733.99 | 0.663 | 2.786 | 889.5 | 0.750 | 0.000 | 16/32 | 1016.53 | D13297 | +2 | GKENNKSAASSKGKITL |
| 12 | 1734.94 | 0.648 | 2.724 | 459.8 | 0.450 | 0.000 | 13/30 | 731.82 | M32066 | | MLLDAIKGGSSDLHFE |
| 13 | 1735.89 | 0.639 | 2.685 | 1461.3 | 0.900 | 0.000 | 19/30 | 1214.40 | M28242 | +1 | FTPESVSRLLEKISAG |
| 14 | 1733.95 | 0.636 | 2.672 | 614.5 | 0.600 | 0.000 | 13/28 | 827.23 | J05110 | | SKPKYNNEVEAKLDV |
| 15 | 1733.99 | 0.632 | 2.658 | 501.7 | 0.525 | 0.000 | 12/30 | 865.03 | M24378 | | MTNTNMHAGVNNSQSQ |
| 16 | 1733.93 | 0.628 | 2.641 | 563.5 | 0.300 | 0.000 | 14/30 | 928.90 | M76547 | | KTDSNGNIKLDCPSLK |
| 17 | 1734.91 | 0.626 | 2.629 | 580.6 | 0.600 | 0.000 | 13/28 | 781.63 | M30149 | +5 | ENLLLNERGYGKLVD |
| 18 | 1734.90 | 0.622 | 2.613 | 756.6 | 0.525 | 0.000 | 17/34 | 992.25 | M33962 | | SGSLSPEHGPIVVHCSAG |
| 19 | 1734.99 | 0.619 | 2.600 | 625.6 | 0.450 | 0.000 | 14/30 | 924.55 | K02670 | | LFVLLAVFIAGLMIGR |
| 20 | 1734.91 | 0.617 | 2.593 | 563.2 | 0.600 | 0.000 | 12/26 | 762.63 | M63585 | +1 | DILDKRLFWAQDGR |

TABLE 1-continued

| No | Mass | $C_n$ | C | $S_p$ | β | ρ | Ions | $I_m$ | Accession No | No of Proteins | Sequence |
|---|---|---|---|---|---|---|---|---|---|---|---|
| 21 | 1735.86 | 0.617 | 2.592 | 491.3 | 0.525 | 0.000 | 13/30 | 743.39 | X67813 | | AQLISAYSLVDPEKAK |
| 22 | 1735.05 | 0.615 | 2.585 | 472.5 | 0.600 | 0.000 | 12/28 | 689.08 | J04120 | +2 | QELVIHIGWIISNNP |
| 23 | 1734.94 | 0.615 | 2.583 | 548.0 | 0.450 | 0.000 | 13/30 | 872.19 | X54240 | | VDESINEDNSVVSLSQ |
| 24 | 1734.63 | 0.609 | 2.561 | 493.4 | 0.525 | 0.000 | 12/28 | 754.92 | X17637 | | DVLANAYRISRQEAQ |
| 25 | 1734.99 | 0.603 | 2.534 | 602.6 | 0.450 | 0.000 | 14/28 | 831.23 | D90034 | | CEDSLDERKIKGVIE |

Mass = calculated candidate peptide mass, $C_n$ = normalized correlation coefficient, C = correlation coefficient, $S_p$ = preliminary score, β = fragment ion continuity, ρ = immonium ions, Ions = number of type b- and y-ions matched out of the total number of fragment ions for candidate sequence, Im = matched fragment intensities, Accession No = genpept accession number, and the candidate peptide sequence, mass = 1734.90, frag tolerance = 0.75, mass tolerance = 1.000.

TABLE 2

| No | Mass | $C_n$ | C | $S_p$ | β | ρ | Ions | $I_m$ | Accession No | No of Proteins | Sequence |
|---|---|---|---|---|---|---|---|---|---|---|---|
| 1 | 1734.90 | 1.000 | 4.203 | 1809.9 | 1.125 | 0.000 | 20/30 | 1277.61 | X17273 | +5 | DLRSWTAADTAAQISK |
| 2 | 1734.86 | 1.000 | 4.203 | 2020.1 | 1.200 | 0.000 | 21/30 | 1311.79 | M84380 | | DLRSWTAADTAAQISQ |
| 3 | 1733.96 | 0.727 | 3.057 | 606.1 | 0.525 | 0.000 | 14/30 | 851.71 | M90516 | | VIFLEDDDVAAVVDGR |
| 4 | 1733.96 | 0.598 | 2.514 | 642.1 | 0.600 | 0.000 | 15/32 | 856.16 | X54637 | | GSSGRNPQASLFGKKAK |
| 5 | 1733.99 | 0.577 | 2.424 | 465.9 | 0.275 | 0.000 | 12/28 | 790.70 | X02598 | | CKLQSGTHCLWTDQL |
| 6 | 1733.93 | 0.558 | 2.347 | 674.2 | 0.450 | 0.000 | 15/32 | 991.85 | Z18330 | +5 | MTQSPATLSVSPGERAT |
| 7 | 1734.12 | 0.554 | 2.329 | 300.2 | 0.225 | 0.000 | 10/28 | 686.18 | Z22658 | | PYVGKELNMIIMLPD |
| 8 | 1734.96 | 0.553 | 2.323 | 447.6 | 0.375 | 0.000 | 13/32 | 801.32 | X02763 | | SSGILSRSSVGPCIRSQ |
| 9 | 1734.94 | 0.549 | 2.307 | 375.1 | 0.225 | 0.000 | 12/30 | 765.57 | J03259 | | FPVDTTELVLTGNNLT |
| 10 | 1735.89 | 0.545 | 2.292 | 544.9 | 0.375 | 0.000 | 14/30 | 849.24 | M18728 | | PASFAWQDDAVISISQ |
| 11 | 1735.86 | 0.543 | 2.281 | 590.0 | 0.450 | 0.000 | 13/28 | 876.39 | J03202 | +1 | ETLENEANNIKMEAE |
| 12 | 1734.91 | 0.542 | 2.276 | 646.1 | 0.450 | 0.000 | 15/30 | 891.21 | X51592 | +2 | KCEIQAALEEAEASLE |
| 13 | 1734.83 | 0.537 | 2.259 | 574.0 | 0.450 | 0.000 | 13/26 | 791.73 | X63575 | +2 | MTNSDFYSKNQRNE |
| 14 | 1733.93 | 0.534 | 2.243 | 500.9 | 0.525 | 0.000 | 13/30 | 758.05 | X15875 | +1 | LTQMADQSTEPALSQI |
| 15 | 1733.97 | 0.532 | 2.235 | 514.3 | 0.600 | 0.000 | 13/30 | 741.72 | S79307 | | LRLSSVTAADTAVYYC |
| 16 | 1735.86 | 0.526 | 2.210 | 377.1 | 0.300 | 0.000 | 12/28 | 676.80 | X12530 | +2 | SEKNSPSTQYCYSIQ |
| 17 | 1733.96 | 0.525 | 2.206 | 518.3 | 0.525 | 0.000 | 15/34 | 770.42 | M25668 | | TAAGGESALAPSVFKQAK |
| 18 | 1734.99 | 0.525 | 2.205 | 360.3 | 0.225 | 0.000 | 12/30 | 735.30 | M81830 | | SSGIRVGSSKRKKSEK |
| 19 | 1733.99 | 0.524 | 2.202 | 376.7 | 0.300 | 0.000 | 12/30 | 724.46 | K03456 | +2 | SEGATPQDLNMMLNIV |
| 20 | 1733.94 | 0.522 | 2.195 | 863.6 | 0.675 | 0.000 | 15/28 | 962.41 | M92269 | +1 | ECLKRQKDRGGDISQ |
| 21 | 1734.94 | 0.520 | 2.187 | 603.4 | 0.525 | 0.000 | 15/36 | 949.64 | M85289 | | AKGSVYIGGAPDVATLTG |
| 22 | 1734.85 | 0.520 | 2.187 | 540.6 | 0.450 | 0.000 | 13/28 | 802.95 | M17081 | +4 | KTDIKVVDRDSEEAE |
| 23 | 1734.99 | 0.516 | 2.167 | 526.1 | 0.750 | 0.000 | 13/28 | 647.52 | L07217 | +5 | IIRSENFTNNAKTII |
| 24 | 1733.99 | 0.515 | 2.166 | 437.6 | 0.450 | 0.000 | 12/30 | 754.47 | X70848 | +3 | VDEKIFCCHGGLSPDL |
| 25 | 1735.67 | 0.510 | 2.143 | 532.9 | 0.450 | 0.000 | 13/30 | 848.14 | M95929 | | SGSDTPQQDNDQLNSE |

EXAMPLE #2

To examine the complexity of the mixture of peptides obtained by proteolysis of the total proteins from *S. cerevisiae* cells, $10^8$ cells were grown and harvested. After lysis, the total proteins were contained in ~9 mL of solution. A 0.5 mL aliquot was removed for proteolysis with the enzyme trypsin. From this solution two microliters were directly injected onto a micro-LC (liquid chromatography) column for MS analysis. In a complex mixture of peptides it is conceivable that multiple peptide ions may exist at the same m/z and contribute to increased background, complicating MS/MS analysis and interpretation. To test the ability to obtain sequence information by MS/MS from these complex mixtures of peptides, ions from the mixture were selected with on-line MS/MS analysis. In no case were the spectra contaminated with fragment ions from other peptides. A partial list of the identified sequences is presented in Table 3.

TABLE 3

| S. cerevisiae Protein | Seq. ID No. | Amino acid Sequence |
|---|---|---|
| enolase | 3 | DPFAEDDWEAWSH |
| hypusine containing protein HP2 | 4 | APEGELGDSLQTAFDEGK |
| phosphoglycerate kinase | 5 | TGGGASLELLEGK |
| BMH1 gene product | 6 | QAFDDAIAELDTLSEESYK |
| pyruvate kinase | 7 | IPAGWQGLDNGPSER |
| phosphoglycerate kinase | 8 | LPGTDVDLPALSEK |
| hexokinase | 9 | IEDDPFENLEDTDDDFQK |
| enolase | 10 | EEALDLIVDAIK |
| enolase | 11 | NPTVEVELTTEK |

The MS/MS spectra presented in Table 1 were interpreted using the described database searching method. This method serves as a data pre-filter to match MS/MS spectra to previously determined amino acid sequences. Pre-filtering the data allows interpretation efforts to be focused on previously unknown amino acid sequences. Results for some of the MS/MS spectra are shown in Table 4. No pre-assigning of sequence ions or manual interpretation is required prior to the search. However, the sequences must exist in the database. The algorithm first pre-processed the MS/MS data and then compared all the amino acid sequences in the database within ±1 amu of the mass of the precursor ion of the MS/MS spectrum. The predicted fragmentation patterns of the amino acid sequences within the mass tolerance were compared to the experimental spectrum. Once an amino acid sequence was within this mass tolerance, a final closeness-of-fit measure was obtained by reconstructing the MS/MS spectra and performing a correlation analysis to the experimental spectrum. Table 4 lists a number of spectra used to test the efficacy of the algorithm.

The computer program described above has been modified to analyze the MS/MS spectra of phosphorylated peptides. In this algorithm all types of phosphorylation are considered such as Thr, Ser, and Tyr. Amino acid sequences are scanned in the database to find linear stretches of sequence that are multiples of 80 amu below the mass of the peptide under analysis. In the analysis each putative site of phosphorylation is considered and attempts to fit a reconstructed MS/MS spectrum to the experimental spectrum are made.

TABLE 4

List of results obtained searching genpept and species specific databases using MS/MS spectra for the respective peptides.

| No. | Mass | Amino Acid Sequence of Peptides used in the Search | Seq. ID No. | Genpept Database | Genpept Database[3] | Species Specific |
|---|---|---|---|---|---|---|
| 1 | 1734.9 | DLRSWTAADTAAQISQ | 12 | 1 | 1 | 1 |
| 2 | 1749 | DLRSWTAADTAAQITQ | 13 | 1 | 1 | 1 |
| 3 | 1186.5 | MATPLLMQALP | 14 | — | — | 13 |
| 4 | 1317.7 | MATPLLMQALP | 14 | 61 | 61 | 17 |
| 5 | 1571.6 | EGVNDNEEGFFSAR[1,2] | 15 | 1* | 1 | 1 |
| 6 | 1571.6 | EGVNDNEEGFFSAR[1,2] | 15 | 1* | 1 | 1 |
| 7 | 1297.5 | DRVYIHPFHL (+2) | 16 | 1 | 1 | 1 |
| 8 | 1297.5 | DRVYIHPFHL (+2) | 16 | 2 | 2 | 2 |
| 9 | 1297.5 | DRVYIHPFHL (+3) | 16 | 1 | 1 | 1 |
| 10 | 1593.8 | VEADVAGHGQDILIR[2] | 17 | 1 | 1 | 1 |
| 11 | 1393.7 | HGVTVLTALGAILK[2] | 18 | 1 | 1 | 1 |
| 12 | 1741.8 | HSGQAEGYSYTDANIK[2] | 19 | 1 | 1 | 1 |
| 13 | 848.8 | HSGQAEGY[2] (+1) | 20 | 1 | 1 | 1 |
| 14 | 723.9 | MAFGGLK[2,3] (+1) | 21 | — | — | — |
| 15 | 636.8 | GATLFK[2] (+1) [QATLFG, KTLFK] | 22 | 1* | 1* | 6 |
| 16 | 524.6 | TEFK (+1) | 23 | 1* | 1* | 5 |
| 17 | 1251.4 | DRNDLLTYLK[1,2] | 24 | 5* | 5 | 1 |
| 18 | 1194.4 | VLVLDTDYKK[2] | 25 | 6 | 6 | 2 |
| 19 | 700.7 | CRGDSY[1] (CGRDSY) | 26 | 3* | 1 | 1 |
| 20 | 700.7 | CRGDSY[1] (+1) | 26 | — | — | 7 |
| 21 | 764.9 | KGATLFK[2] | 27 | 3 | 3 | 1 |
| 22 | 1169.3 | TGPNLHGLFGR | 28 | 1 | 1 | 1 |
| 23 | 1047.2 | DRVYIHPF | 29 | — | — | 7 |
| 24 | 1139.3 | TLLVGESATTF (+1) | 30 | 1 | 1 | 1 |
| 25 | 1189.4 | RNVIPDSKY | 31 | 1 | 1 | 1 |
| 26 | 613.7 | SSPLPL (+1) | 32 | 2 | 4 | 2 |
| 27 | 1323.5 | LARNCQPNYW (C = 161.17) | 33 | 1 | 1 | 1 |
| 28 | 2496.7 | AQSMGFINEDLSTSAQALMSDW | 34 | 1 | 1 | 1 |
| 29 | 1551.8 | VTLIHPIAMDDGLR | 35 | 3 | 3 | 1 |
| 30 | 1803.0 | GGDTVTLNETDLTQIPK | 36 | 2 | 2 | 1 |
| 31 | 1172.4 | VGEEVEIVGIK | 37 | 1 | 1 | 1 |
| 32 | 2148.5 | GWQVPAFTLGGEATDIVVMR | 38 | 1 | 1 | 1 |
| 33 | 2553.9 | VASISLPTSCASAGTQCLISGWGNTK[1] | 39 | — | 1 | 1 |
| 34 | 1154.3 | SSGTSYPDVLK[1] | 40 | — | 3 | 1 |
| 35 | 1174.5 | TLNNDIMLIK | 41 | 1 | 1 | 1 |
| 36 | 2274.6 | SIVHPSYNSNTLNNDIMLIK[1] | 42 | — | 2 | 1 |

[1]not present in the genpept database
[2]sequence appended to the human database, not originally in human database
[3]amino acid sequences added to database
(—) not in the top 100 answers
*peptide of similar sequence identified

EXAMPLE #3

Much of the information generated by the genome projects will be in the form of nucleotide sequences. Those stretches of nucleotide sequence that can be correlated to a gene will be translated to a protein sequence and stored in a specific database (genpept). The un-translated nucleotide sequences represent a wealth of data that may be relevant to protein sequences. The present invention will allow searching the nucleotide database in the same manner as the protein sequence databases. The procedure will involve the same algorithmic approach of cycling through the nucleotide sequence. The three-base codon will be converted to a protein sequence and the mass of the amino acids summed. To cycle through the nucleotide sequence, a one-base increment will be used for each cycle. This will allow the determination of an amino acid sequence for each of the three reading frames in one pass. For example, an MS/MS spectrum is generated for the sequence Asp-Leu-Arg-Ser-Trp-Thr-Ala [Seq. ID No. 43] ((M+H)+=848) the algorithm will search the nucleotide sequence in the following manner.

|  |  |  |  |  |  |  |  |  |  |  | Seq. ID No. |
|---|---|---|---|---|---|---|---|---|---|---|---|
| Nucleotide sequence from the database. | | | | | | | | | | | |
| nucleotides GCG AUC UCC | | | GGU | CUU | GGA | CUG | CUC | | | | 44 |
| First pass through the sequence. | | | | | | | | | | | |
| nucleotides GCG AUC UCC | | | GGU | CUU | GGA | CUG | CUC | | Mass | | 44 |
| amino acids Ala Ile Ser | | | Gly | Leu | Gly | Leu | Leu | | 743 | | 45 |
| Second pass through the sequence. | | | | | | | | | | | |
| nucleotides G CGA UCU | | | CCG | GUC | UUG | GAC | UGC | UC | Mass | | 44 |
| amino acids Arg Ser | | | Pro | Val | Leu | Gly | .Leu | | 741 | | 46 |
| Third pass through the sequence. | | | | | | | | | | | |
| nucleotides GC GAU CUC | | | CGG | UCU | UGG | ACU | GCU | C | Mass | | 44 |
| amino acids Asp Leu | | | Arg | Ser | Trp | Thr | Ala | | 848 | | 43 |
| Fourth pass through the sequence. | | | | | | | | | | | |
| nucleotides GCG AUC UCC | | | GGU | CUU | GGA | CUG | CUC | | Mass | | 44 |
| amino acids Ile Ser | | | Gly | Leu | Gly | Leu | Leu | | 672 | | 45 |

As the sequence of amino acids match the mass of the peptide the predicted sequence ions will be compared to the MS/MS spectrum. From this point on the scoring and reporting procedures for the search will be the same as for a protein sequence database.

In light of the above description, a number of advantages of the present invention can be seen. The present invention permits correlating mass spectra of a protein, peptide or oligonucleotide with a nucleotide or protein sequence database in a fashion which is relatively accurate, rapid, and which is amenable to automation (i.e., to operation without the need for the exercise of human judgment). The present invention can be used to analyze peptides which are derived from a mixture of proteins and thus is not limited to analysis of intact homogeneous proteins such as those generated by specific and known proteolytic cleavage.

A number of variations and modifications of this invention can also be used. The invention can be used in connection with a number of different proteins or peptide sources and it is believed applicable to any analysis using mass spectrometry and proteins. In addition to the examples described above, the present invention can be used for, for example, monitoring fermentation processes by collecting cells, lysing the cells to obtain the proteins, digesting the proteins, e.g. in an enzyme reactor, and analyzing by Mass spectrometry as noted above. In this example, the data could be interpreted using a search of the organism's database (e.g., a yeast database). As another example, the invention could be used to determine the species of organism from which a protein is obtained. The analysis would use a set of peptides derived from digestion of the total proteins. Thus, the cells from the organism would be lysed, the proteins collected and digested. Mass spectrometry data would be collected with the most abundant peptides. A collection of spectra (e.g., 5 to 10 spectra) would be used to search the entire database. The spectra should match known proteins of the species. Since this method would use the most abundant proteins in the cell, it is believed that there is a high likelihood the sequences for these organisms would be sequenced and in the database. In one embodiment, relatively few cells could be used for the analysis (e.g., on the order of $10_4$–$10^5$).

The present invention can be used in connection with diagnostic applications, such as described for Example No. 2 above. Another example would involve identifying virally infected cells. Success of such an approach is believed to depend on the relative abundance of the viral proteins versus the cellular proteins, at least using present equipment. If an antibody were produced to a specific region of a protein common to certain pathogens, the mixture of proteins could be partially fractionated by passing the material over an immunoaffinity column. Bound proteins are eluted and digested. Mass spectrometry generates the data to search a database. One important element is finding a general handle to pull proteins from the cell. This approach could also be used to analyze specific diagnostic proteins. For example, if a certain protein variant is known to be present in some form of cancer or genetic disease, an antibody could be produced to a region of the protein that does not change. An immunoaffinity column could be constructed with the antibody to isolate the protein away from all the other cellular proteins. The protein would be digested and analyzed by tandem mass spectrometry. The database of all the possible mutations in the protein could be maintained and the experimental data analyzed against this database.

One possible example would be cystic fibrosis. This disease is characterized by multiple mutations in CFTR protein. One mutation is responsible for about 70% of the cases and the other 30% of the cases result from a wide variety of mutations. To analyze these mutations by genetic testing would require many different analyses and probes. In the assay described above, the protein would be isolated and analyzed by tandem mass spectrometry. All the mutations in the protein could be identified in an assay based on structural information. The database used would preferably describe all the known mutations. Implementation of this approach is believed to involve significant difficulties. The amount of protein required could be so large that it would be impractical to obtain from a patient. This problem may be overcome as the sensitivity of mass spectrometry improves in the future. A protein such as CFTR is a transmembrane protein, which are typically very difficult to manipulate and digest. The approach described could be used for any diagnostic protein. The data would be highly specific and the data analysis essentially automated.

It is believed that the present invention can be used with any size peptide. The process requires that peptides be fragmented and there are methods for achieving fragmentation of very large proteins. Some such techniques are described in Richard D. Smith et, al., "Collisional Activation and Collision-Activated Dissociation of Large Multiply Charged Polypeptides and Proteins Produced by Electrospray Ionization" *J. American Society for Mass Spectrometry* (1990) Vol. I, pp. 53–65. It is believed the present method could be used to analyze data derived from intact proteins. Although, as noted above, it is believed that there is no theoretical or absolute practical limit to the size of peptides that could be analyzed according to this invention, analysis using the present invention has been performed on peptides at least in the size range from about 400 amu (4 residues) to about 2500 amu (26 residues).

Although in one described embodiment, candidate subsequences are identified and fragment spectra are predicted as they are needed, at the time of doing the analysis. It would be possible, if sufficient computational resources and storage facilities are available to perform some or all of the calculations needed for candidate sequence identification (such as calculation of sub-sequence masses) and/or spectra prediction (such as calculation of fragment masses) and storage of these items in a database so that some or all of these items can be looked up rather than calculated each time they are needed.

While the present invention has been described by way of the preferred embodiment and certain variations and modifications, other variations and modifications of the present invention can also be used, the invention being described by the following claims.

What is claimed is:

1. A method for correlating a mass spectrum of a peptide fragment from a first peptide with amino acid sequences derived from a database of sequences, comprising:

storing data representing a first mass spectrum of a plurality of fragments of at least the first peptide;

calculating a plurality of predicted mass spectra of at least a portion of a plurality of said amino acid sequences in said database of sequences; and calculating at least a first measure for each of said plurality of predicted mass spectra, said first measure being an indication of the closeness-of-fit between said first mass spectrum and each of said plurality of mass spectra.

2. A method, as claimed in claim 1, wherein said first mass spectrum is provided from a tandem mass spectrometer device.

3. A method, as claimed in claim 2, wherein the tandem mass spectrometer is one of a triple quadrupole mass spectrometer, a Fourier-transform cyclotron resonance mass spectrometer, a tandem time-of-flight mass spectrometer and a quadrupole ion trap mass spectrometer.

4. A method, as claimed in claim 1, wherein said database of sequences is a database of amino acid sequences of a plurality of proteins.

5. A method, as claimed in claim 1, wherein said database of sequences is a nucleotide database.

6. A method, as claimed in claim 1, further comprising the steps of selecting a first plurality of sub-sequences from said database of sequences, and calculating at least one predicted mass spectrum for each of said selected first plurality of sub-sequences.

7. A method, as claimed in claim 1, wherein said step of calculating a first measure includes selecting those values from said first mass spectrum having an intensity greater than a predetermined threshold.

8. A method, as claimed in claim 1, further comprising normalizing said first spectrum prior to said step of calculating at least a first measure.

9. A method, as claimed in claim 1, wherein said step of calculating a plurality of predicted mass spectra includes calculating predicted mass spectra for only a portion of said sequence database.

10. A method, as claimed in claim 9, wherein said first peptide is derived from a protein which is obtained from a first organism and wherein said protein of said sequence database is the portion containing sequences for proteins found in said first organism.

11. A method, as claimed in claim 2 wherein a first mass spectrometer of said tandem mass spectrometer device is used to separate-out a first component having a first mass, an activation device of said tandem mass spectrometer device is used to fragment said first component and a second mass spectrometer of said tandem mass spectrometer device is used provide said first mass spectrum.

12. A method, as claimed in claim 1, wherein said first peptide is isolated by chromatography.

13. A method, as claimed in claim 1, wherein said data representing said first mass spectrum includes a plurality of mass-charge pairs.

14. A method, as claimed in claim 1, wherein said step of calculating predicted mass spectra comprises:

deriving a plurality of masses from portions of said plurality of sequences, each mass equal to the mass of a peptide fragment which corresponds to a portion of a sequence in said plurality of sequences;

selecting those masses, among said plurality of masses, which are within a predetermined mass tolerance of the mass of said first peptide and storing an indication of which portion of which sequence each of said selected masses corresponds to, to provide a plurality of candidate sequence portions; and calculating a plurality of mass-charge pairs for each of said candidate sequence portions, each of said mass-charge pairs having a mass substantially equal to the mass of a peptide fragment corresponding to a portion of one of said candidate sequence portions.

15. A method, as claimed in claim 1, wherein said first measure comprises a correlation coefficient.

16. A method, as claimed in claim 1, wherein said step of calculating a first measure comprises:

calculating a preliminary score for each of said plurality of candidate sequence portions;

identifying a plurality of primary candidate portions which have a preliminary score which is greater than at least one candidate sequence which is not identified as a primary candidate portion; and calculating a correlation coefficient for each of said primary candidate portions.

17. A method, as claimed in claim 8, wherein each of said plurality of mass spectra and said first mass spectrum includes a plurality of mass-charge pairs, each mass-charge pair having an intensity value, and further comprising the step of identifying, for each of said plurality of mass spectra, a set of matched fragments which have less than a predetermined difference from corresponding fragments in said first mass spectrum; and wherein said preliminary score is the number of fragments of a predicted mass spectrum in said set of matched fragments multiplied by the sum of the intensity values for the mass-charge pairs corresponding to said matched fragments.

18. A method for determining whether a peptide in a mixture of proteins is homologous to a portion of any of a plurality of proteins specified by an amino acid sequence in a database of sequences, comprising:

using a tandem mass spectrometer to receive a plurality of peptides obtained from said mixture of proteins, to select at least a first peptide from said mixture of peptides, to fragment said first peptide and to generate a peptide fragment mass spectrum;

storing data representing said first mass spectrum; and correlating said mass spectrum with an amino acid sequence in said database of sequences, to determine the correspondence of a protein specified in said sequence database with a protein in said mixture of proteins.

19. A method, as claimed in claim 18, wherein said step of correlating includes predicting at least one mass spectrum from said amino acid sequence.

* * * * *

UNITED STATES PATENT AND TRADEMARK OFFICE
CERTIFICATE OF CORRECTION

PATENT NO. : 5,538,897

DATED : July 23, 1996

INVENTOR(S) : John R. Yates, III and Jimmy K. Eng

It is certified that error appears in the above-identified patent and that said Letters Patent is hereby corrected as shown below:

On the title page, item [75],
In inventor James K. Eng's name, please delete "James" and substitute therefore -- Jimmy --.

Signed and Sealed this

Fourth Day of March, 1997

Attest:

BRUCE LEHMAN

*Attesting Officer*    Commissioner of Patents and Trademarks